(12) United States Patent
Aboul-Hosn et al.

(10) Patent No.: US 6,935,344 B1
(45) Date of Patent: *Aug. 30, 2005

(54) METHODS AND SYSTEMS FOR PROVIDING RIGHT AND/OR LEFT HEART SUPPORT DURING CARDIAC SURGERY

(75) Inventors: Walid N. Aboul-Hosn, Fair Oaks, CA (US); William R. Kanz, Sacramento, CA (US)

(73) Assignee: A-Med Systems, Inc., W. Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/481,730

(22) Filed: Jan. 11, 2000

Related U.S. Application Data

(63) Continuation-in-part of application No. PCT/US99/19537, filed on Aug. 27, 1999, and a continuation-in-part of application No. PCT/US99/13666, filed on Jun. 18, 1999, and a continuation-in-part of application No. 09/231,320, filed on Jan. 13, 1999, now Pat. No. 6,532,964, and a continuation-in-part of application No. 08/933,566, filed on Sep. 19, 1997.

(60) Provisional application No. 60/152,249, filed on Sep. 3, 1999, provisional application No. 60/115,786, filed on Jan. 13, 1999, provisional application No. 60/113,727, filed on Dec. 23, 1998, and provisional application No. 60/098,118, filed on Aug. 27, 1998.

(51) Int. Cl.$^7$ ............................................. A61B 19/00
(52) U.S. Cl. ................................................... 128/898
(58) Field of Search ........................................ 128/898

(56) References Cited

U.S. PATENT DOCUMENTS 3,626,947 A    12/1971   Sparks
3,847,784 A    11/1974   Rafferty
3,995,617 A    12/1976   Watkins et al.

(Continued)

FOREIGN PATENT DOCUMENTS

| CA | 2037622 | 9/1991 |
|----|---------|--------|
| EP | 0 445 782 | 9/1991 |
| EP | 0 478 635 | 4/1992 |

(Continued)

*Primary Examiner*—David H. Willse
*Assistant Examiner*—William Matthews
(74) *Attorney, Agent, or Firm*—Ryan Kromholz & Manion, S.C.

(57) ABSTRACT

The present invention relates to systems and methods for performing beating heart surgery involving the step of maintaining at least partial blood flow through a protected blood flow path within the right and/or left side of the heart during surgery. The protected blood flow path may be established by positioning one or more conduits within at least a portion of the right and/or left sides(s) of the heart. In a first system, at least partial blood flow may be maintained through the protected blood flow path by the pumping action of a blood pump communicatively coupled to the conduit. In a second system, at least partial blood flow is maintained through the protected blood flow path by the pumping action of the beating heart itself. The systems are therefore capable of maintaining at least partial blood flow through the right and/or left side(s) of the heart, even during periods when the cardiac output becomes compromised. The patient's lung(s) may be used at all times utilized for blood oxygenation during heart surgery, thereby avoiding the need for artificial cardiopulmonary bypass (CPB) circuits and the attendant disadvantages of CPB.

3 Claims, 18 Drawing Sheets

U.S. PATENT DOCUMENTS

| | | | |
|---|---|---|---|
| 4,086,665 A | | 5/1978 | Poirier |
| 4,108,161 A | | 8/1978 | Samuels et al. |
| 4,118,806 A | | 10/1978 | Poirier et al. |
| 4,173,981 A | | 11/1979 | Mortensen |
| 4,548,597 A | | 10/1985 | Nelson |
| 4,625,712 A | | 12/1986 | Wampler |
| 4,704,121 A | | 11/1987 | Moise |
| 4,753,221 A | | 6/1988 | Kensey et al. |
| 4,769,031 A | | 9/1988 | McGough et al. |
| 4,817,586 A | | 4/1989 | Wampler |
| 4,846,152 A | | 7/1989 | Wampler et al. |
| 4,898,518 A | | 2/1990 | Hubbard et al. |
| 4,944,722 A | | 7/1990 | Carriker et al. |
| 4,955,856 A | | 9/1990 | Phillips |
| 4,985,014 A | * | 1/1991 | Orejola ................. 600/16 |
| 5,019,102 A | | 5/1991 | Hoene |
| 5,061,256 A | | 10/1991 | Wampler |
| 5,112,349 A | | 5/1992 | Summers |
| 5,295,958 A | | 3/1994 | Shturman |
| 5,376,114 A | * | 12/1994 | Jarvik ................. 623/3.3 |
| 5,449,342 A | | 9/1995 | Hirose et al. |
| 5,478,309 A | | 12/1995 | Sweezer et al. |
| 5,599,329 A | | 2/1997 | Gabbay |
| 5,647,358 A | | 7/1997 | Vilasi |
| 5,688,245 A | | 11/1997 | Runge |
| 5,718,678 A | | 2/1998 | Fleming |
| 5,727,569 A | | 3/1998 | Benetti et al. |
| 5,741,234 A | | 4/1998 | Aboul-Hosn |
| 5,746,709 A | | 5/1998 | Rom et al. |
| 5,755,784 A | | 5/1998 | Jarvick |
| 5,766,209 A | | 6/1998 | Devonec |
| 5,785,686 A | | 7/1998 | Runge |
| 5,827,220 A | | 10/1998 | Runge |
| 5,851,174 A | | 12/1998 | Jarvick |
| 5,921,913 A | | 7/1999 | Siess |
| 5,965,089 A | | 10/1999 | Jarvick et al. |
| 5,972,020 A | * | 10/1999 | Carpentier et al. ......... 606/208 |
| 6,083,260 A | | 7/2000 | Aboul-Hosn |
| 6,086,570 A | | 7/2000 | Aboul-Hosn et al. |
| 6,113,536 A | | 9/2000 | Aboul-Hosn et al. |
| 6,123,725 A | | 9/2000 | Aboul-Hosn |
| 6,152,704 A | | 11/2000 | Aboul-Hosn et al. |
| 6,210,133 B1 | | 4/2001 | Aboul-Hosn et al. |
| 6,210,397 B1 | | 4/2001 | Aboul-Hosn et al. |
| 6,228,063 B1 | | 5/2001 | Aboul-Hosn |
| 6,234,960 B1 | | 5/2001 | Aboul-Hosn et al. |
| 6,287,319 B1 | | 9/2001 | Aboul-Hosn et al. |
| 6,295,877 B1 | | 10/2001 | Aboul-Hosn et al. |
| 6,395,026 B1 | * | 5/2002 | Aboul-Hosn et al. ....... 606/208 |
| 6,532,964 B2 | | 3/2003 | Aboul-Hosn et al. |
| 2003/0023201 A1 | | 1/2003 | Aboul-Hosn et al. |
| 2003/0205233 A1 | | 11/2003 | Aboul-Hosn et al. |

FOREIGN PATENT DOCUMENTS

| | | |
|---|---|---|
| EP | 0 629 412 | 12/1994 |
| EP | 0 659 443 | 6/1995 |
| EP | 768 091 | 4/1997 |
| EP | 0 280 225 | 8/1998 |
| RU | 286 145 | 1/1971 |
| WO | WO 89/10763 | 11/1989 |
| WO | WO 96/18358 | 6/1996 |
| WO | WO 97/02850 | 6/1997 |
| WO | WO 97/37698 | 10/1997 |
| WO | WO 98/14225 | 4/1998 |
| WO | WO 98/53864 | 12/1998 |
| WO | WO 99/02204 | 1/1999 |
| WO | WO 99/59652 | 11/1999 |
| WO | WO 99/65546 | 12/1999 |
| WO | WO 00/12148 | 3/2000 |
| WO | WO 00/18448 | 4/2000 |
| WO | WO 00/19097 | 4/2000 |
| WO | WO 00/69489 | 11/2000 |

\* cited by examiner

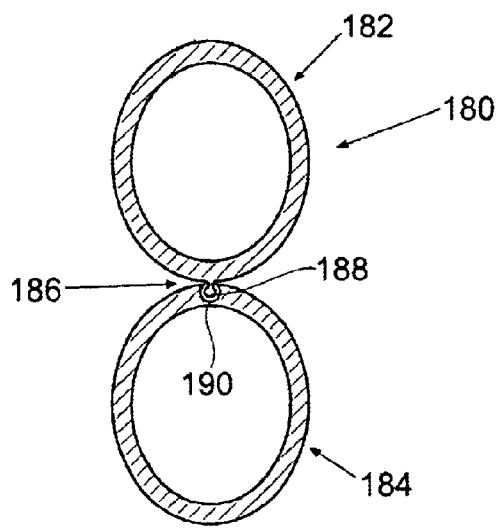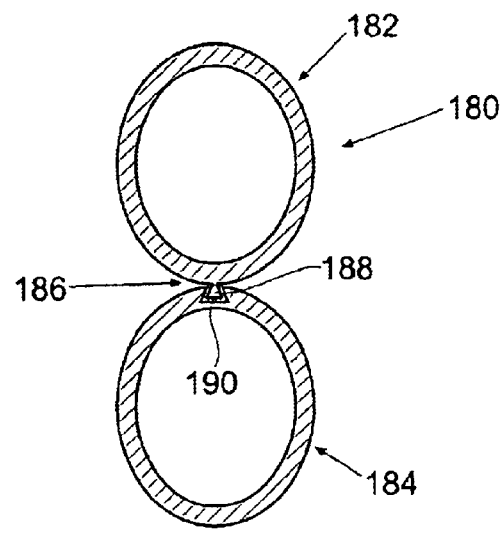
Fig. 16A  Fig. 16B
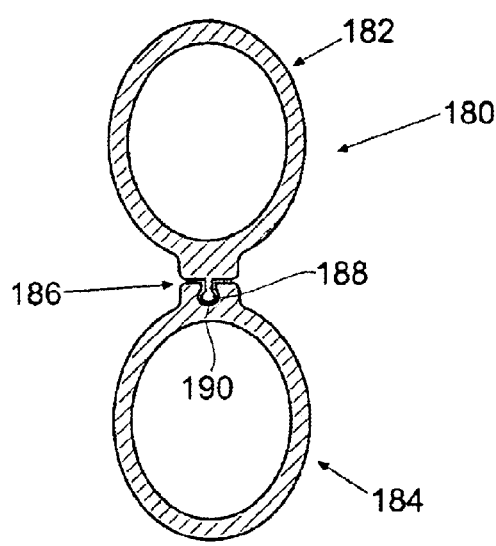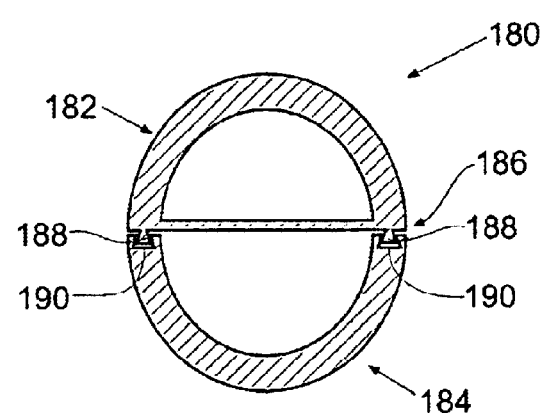
Fig. 16C  Fig. 16D

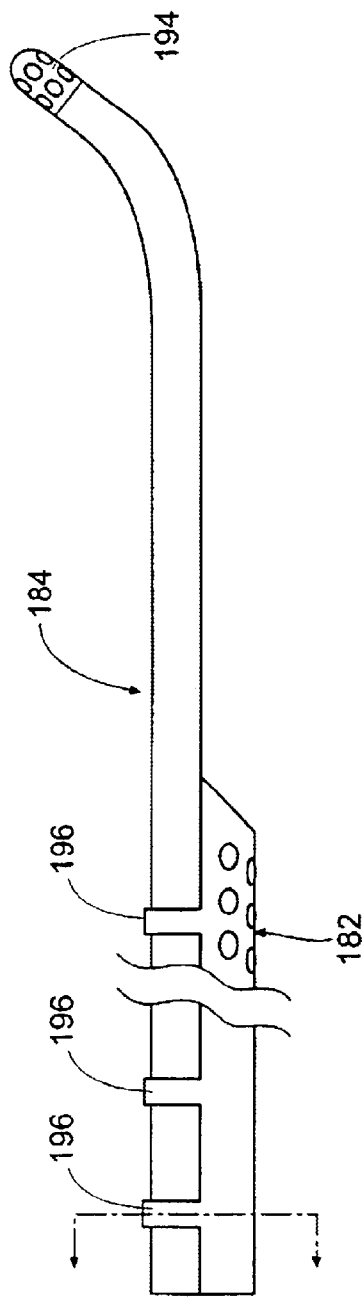
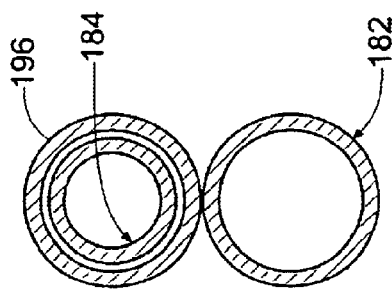
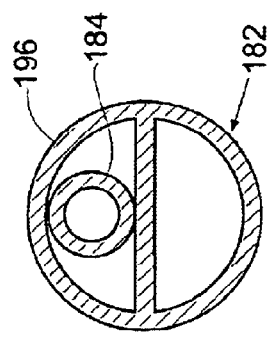
Fig. 17
Fig. 18B
Fig. 18A

METHODS AND SYSTEMS FOR PROVIDING RIGHT AND/OR LEFT HEART SUPPORT DURING CARDIAC SURGERY

REFERENCE TO RELATED APPLICATIONS

This application is a continuation in part of the following: U.S. patent application Ser. No. 09/231,320, filed Jan. 13, 1999now U.S. Pat. No. 6,532,964 (which is a continuation-in-part of U.S. patent application Ser. No. 09/079,836, filed May 15, 1998, now U.S. patent application Ser. No. 6,395,026), U.S. patent application Ser. No. 09/462,656 (which is 371of Int'l patent applicatin Ser. No. PCT/US97/18674, filed Oct. 14, 1997, (which is a continuation-in-part of U.S. patent application Ser. No. 08/933,566, filed Sep. 19, 1997), now U.S. patent application Ser. No. 6,083,260, (which is a continuation-in part of U.S. patent App. Ser. No. 08/891, 4546, filed Jul. 11, 1997, now. U.S. patent application Ser. No. 6,123,725), Int'l Patent App. Ser. No. PCT/US99/13666, filed Ju. 18, 1999 (which is a continuation-in-part of U.S. Patent App. Ser. No. 09/099,713, filed Jun. 19, 1998, now abandoned, and which claims benefit to claims priority to U.S. Provisional Patent App. Ser. No. 60/113,727, filed Dec. 23, 1998), and Int'l Patent App. Ser. No. PCT/US99/ filed Aug. 27, 1999 (which claims benefit to U.S.Provisional Patent App. Ser. No. 60/098,118, filed Aug. 27, 1998). This application claims benefit to U.S. Provisional Patent App. Ser. No. 60/115,786, filed Jan. 1, 1999, and U.S. Provisional Patent App. Ser. No. 60/152,249, filed Sep. 3, 1999.

BACKGROUND OF THE INVENTION

I. Field of the Invention

The present invention involves met hods and systems for performing heart surgery. More particularly, the present invention is directed to methods and systems for providing right and/or left heart support during beating heart surgery.

II. Discussion of the Prior Art

Major heart surgery is oftentimes accomplished by procedures that require full car diopulmonary bypass (CPB) through the use of artificial heart-lung machines and complete cessation of cardiopulmonary activity. While the average mortality rate with this type of procedure is low, it is nonetheless associated with a complication rate that is often much higher compared to when cessation of the heart and CPB are not required. The use of CPB continues to represent a major assault on a host of body systems. For example, there is noticeable degradation of mental faculties following such surgeries in a significant percentage of patients who undergo coronary artery bypass grafting (CABG) procedures. The CABG procedure generally involves open chest surgical techniques to treat diseased vessels. During this procedure, the sternum of the patient is cut in order to spread the chest apart and provide access to the heart. During surgery the heart is stopped, and by the use of CPB blood is diverted from the lungs to an artificial oxygenator. In general CABG procedures, a source of arterial blood is then connected to a coronary artery downstream from the occlusion. The source of blood is often an internal mammary artery, and the target coronary artery is typically among the anterior or posterior arteries which may be narrowed or occluded. The degradation of mental faculties resulting from CABG procedures is commonly attributed to cerebral arterial blockage and emboli from debris in the blood generated by the use of CPB. At the same time, the dramatic increase in the life expectancy of the general population has resulted in patients that are more likely to be older and in poor health, with less cardiovascular, systemic, and neurologic reserve needed to recover from the trauma caused by the use of CPB. As a consequence, inflammatory, hemostatic, endocrinologic, and neurologic stresses are tolerated to a much lesser degree by a significant number of patients today, and play a more significant role in CPB-induced morbidity.

The combined statistics of postoperative morbidity and mortality continue to illustrate the shortcomings of CPB. The extracorporeal shunting and artificially induced oxygenation of blood activates a system wide roster of plasma proteins and blood components in the body including those that were designed to act locally in response to infection or injury. When these potent actors are disseminated throughout the body without normal regulatory controls, the entire body becomes a virtual battleground. The adverse hemostatic consequences of CPB also include prolonged and potentially excessive bleeding. CPB-induced platelet activation, adhesion, and aggregation also contribute to a depletion in platelet number, and is further compounded by the reversibly depressed functioning of platelets remaining in circulation. The coagulation and fibrinolytic systems both contribute to hemostatic disturbances during and following CPB. However, the leading cause of morbidity and disability following cardiac surgery is cerebral complications. Gaseous and solid micro and macro emboli, and less often perioperative cerebral hypoperfusion, produce neurologic effects ranging from subtle neuropsychologic deficits to fatal stroke. Advances in computed tomography, magnetic resonance imaging, ultrasound, and other imaging and diagnostic techniques have added to the understanding of these complications. But with the possible exception of perioperative electroencephalography, these technologies do not yet permit real time surgical adjustments that are capable of preventing emboli or strokes in the making. Doppler and ultrasound evaluation of the carotid artery and ascending aorta, and other diagnostic measures, can help identify surgical patients at elevated risk for stroke and are among the growing list of pharmacologic and procedural measures for reducing that risk.

CPB also affects various endocrine systems, including the thyroid gland, adrenal medulla and cortex, pituitary gland, pancreas, and parathyroid gland. These systems are markedly affected not only by inflammatory processes, but also by physical and biochemical stresses imposed by extracorporeal perfusion. Most notably, CPB is now clearly understood to induce euthyroid-sick syndrome which is marked by profoundly depressed triiodothyronine levels persisting for days following cardiothoracic surgery. The efficacy of hormone replacement regimens to counteract this effect are currently undergoing clinical investigation. By contrast, levels of the stress hormones epinephrine, norepinephrine, and cortisol are markedly elevated during and following CPB, and hyperglycemia is also possible.

Beating heart bypass surgery has been recognized as desirable because it has the possibility of avoiding the necessity of placing the patient on a full CPB system. However, attempts at beating heart bypass surgery have met with limited success and have essentially been limited to surgery on the anterior heart vessels due to problems which develop when the beating heart is lifted or displaced from its normal all position in order to perform the beating heart surgery. Typically when the beating heart is lifted or manipulated in order to provide surgical access to posterior heart vessels, a number of difficulties are encountered. When the beating heart is lifted and manipulated, the right side of the heart tends to collapse, particularly the right auricle or atrium and frequently the right ventricle and/or pulmonary artery. When the right side of the heart collapses, pulmonary blood flow either ceases or becomes inadequate, thus forcing the use of CPB. Another difficulty encountered is that, even if the right side of the heart does not collapse, the pulmonary artery and/or the pulmonary vein frequently become crimped or kinked thus also impeding the pulmonary blood flow. Similarly, during the lifting and manipulation of the beating heart for lateral or posterior access, the left side of the heart, particularly the left auricle or left atrium can also collapse or partially collapse, thus impeding aortic circulatory blood flow. Further, when the beating heart is lifted or manipulated for beating heart surgery access or during catheterization or cannulation procedures, the heart may lapse into arrhythmia or disrhythmia or may arrest at least a portion of the time or most of the time that the surgery is being performed thus likewise impeding pulmonary blood flow and arterial circulatory blood flow. As a result, patients undergoing beating heart surgery are at risk of having to be placed on CPB on an emergency basis in the event that the pulmonary and/or circulatory blood flow is compromised during the surgery, which presents the CPB-induced side effects previously described.

The medical community is currently performing more beating heart bypass surgery in an effort to avoid the use of full CPB. The need is increasing for apparatus systems, methods and associated equipment to enhance the capability and versatility of beating heart surgery and to avoid CPB procedures in any heart surgery. The current trend toward thoracoscopic methods of performing bypass surgery, without opening the chest cavity, have resulted in limited success and applicability primarily due to the limited number of heart vessels which can be accessed through thoracoscopic methods. A major limitation of thorascopic bypass surgery methods is due to the fact that only the anterior heart vessels are accessible for surgery. More importantly, even open chest surgery providing full access to the heart also requires CPB when bypass surgery is performed on the lateral or posterior vessels of the heart, due to the fact that in conventional procedures the heart must be stopped when it is lifted or rotated from its normal position and manipulated for surgical access to the various heart vessels.

The present invention addresses this need by providing systems and methods for performing cardiac surgery that eliminate, or at least reduce, the need for full CPB.

SUMMARY OF THE INVENTION

The present invention provides methods and systems for performing cardiac surgery wherein the patient's lungs are used for blood oxygenation, thereby avoiding the need for CPB or other external blood oxygenation equipment or procedure. The present invention accomplishes this goal by maintaining at least partial blood flow through a protected blood flow path within the right and/or left side(s) of a beating heart to ensure sufficient pulmonary blood flow to the lungs and/or circulatory blood flow throughout the body during beating heart cardiac surgery. In reference to this invention, the "right side" of the heart refers to and includes the vena cava veins (superior and inferior), the right atrium, the right ventricle, the pulmonary artery and any combination or all thereof. The "right side" of the heart provides the pulmonary blood flow to the lungs. The "left side" of the heart refers to and includes the pulmonary veins, the left atrium, the left ventricle, the aorta and any combination or all thereof The "left side" of the heart provides the circulatory blood flow to the body. The terms "pulmonary artery" and "pulmonary vein" include all branches thereof, and the term "aorta" includes the aortic vessels which are near the heart and are exposed or manipulated during open chest cardiac surgery or are utilized during minimally invasive cardiac surgery. As will be explained in greater detail below, in accordance with the present invention the protected blood flow path may be established by positioning one or more conduits within at least a portion of the right and/or left sides(s) of the heart, and at least partial blood flow may be maintained through the protected blood flow path by the pumping action of a blood pump communicatively coupled to the conduit or, alternately, by the pumping action of the beating heart itself.

In an important aspect, the present invention ensures sufficient pulmonary and/or circulatory blood flow during beating heart surgery regardless of any compromise in cardiac output or function experienced during beating heart surgery. Generally speaking, such compromise conditions include any situation where the cardiac output of the beating heart is diminished or disrupted from normal levels. As noted above, the cardiac output of a beating heart can become compromised in a multitude of ways during beating heart surgery. For example, when the beating heart is lifted and manipulated to provide surgical access to posterior or lateral heart vessels, portions of the right and/or left side of the heart may collapse, thereby causing the pulmonary and/or circulatory blood flow to either cease or become inadequate. Even if collapse does not occur, portions of the right and/or left side of the heart may nonetheless become crimped or kinked (particularly the pulmonary artery and/or the pulmonary vein) and thereby impede or cease the pulmonary and/or circulatory blood flow during beating heart surgery. The cardiac output of the heart may also become compromised if the heart lapses even briefly into arrhythmia, disrhythmia, or arrest during beating heart surgery. Up until now, the above-identified compromise conditions place patients undergoing beating heart surgery at risk of being placed on CPB on an emergency basis in the event that the pulmonary and/or circulatory blood flow is compromised during the surgery. By maintaining at least partial blood flow through the right and/or left sides of the heart during beating heart surgery, the present invention removes this risk and thus avoids the host of adverse side-effects associated with CPB.

The present invention provides, generally speaking, two types of systems for carrying out the methods of this invention, which systems may be selected and employed (individually or in combination) in the right and/or left side(s) of the heart to meet the needs of a particular beating heart surgical procedure. The first system involves a pump and cannula system for selectively augmenting the heart's natural pumping ability during beating heart surgery to ensure sufficient pulmonary and/or circulatory blood flow, thereby avoiding the need for CPB. The second system involves one or more conduits, such as cannulas and/or stents, positioned within the heart to establish a protected blood flow path such that the heart's natural pumping activity will maintain at least partial blood flow therethrough during beating heart surgery, thereby ensuring sufficient pulmonary and/or circulatory blood flow and thus avoiding the need for CPB.

The first system for carrying out the methods of the present invention may take a variety of different forms. Generally speaking, the cannula is positioned to establish a protected blood flow path within a portion of the heart and the pump is selectively operated to maintain at least partial blood flow therethrough during beating heart surgery. For right heart support, the cannula may extend through the tricuspid valve and/or pulmonary valve into the pulmonary artery. For left heart support, the cannula may extend through the bicuspid valve and/or aortic valve into the aorta. In either embodiment, the pump is communicatively coupled to the cannula to selectively (i.e. automatically or on-demand) transport blood past the valve(s) through which the cannula passes to augment the pumping ability of the right and/or left side of the heart. The pump may be adapted as a miniaturized blood pump so it can be positioned close to the heart, either in the open chest cavity or at least in the sterile surgical field, thus providing a minimum priming volume. Alternatively, the cannula can also be adapted to be inserted into the heart in closed chest procedures through the chest wall as part of a thoracoscopic procedure, through the femoral vein, the jugular vein or any appropriate access point in the venous system. In these instances, the pump is adapted to be positioned as close to the body insertion point as possible in order to keep priming volume to a minimum; for that reason thoracoscopic or jugular access is preferred when a closed chest procedure is elected. The pump may also comprise an intravascular pump dimensioned to be positioned within the heart itself, having a priming volume of approximately zero. The pump, in all embodiments, is preferably variable output and controlled (automatically or on-demand) in response to one of a variety of appropriate parameters, including but not limited to blood pressure, blood flow, blood oxygen level, and/or blood $CO_2$ level.

In all embodiments, the pump and cannula system may be used in both the right and left sides when bypass surgery is initiated. The pump and cannula system of the present invention is particularly useful during beating heart surgery to overcome or prevent situations where cardiac output or outflow may become compromised. As noted above, these situations may stem from, but are not necessarily limited to, instances when the heart is lifted, rotated or otherwise manipulated to access lateral or posterior blood vessels, when the heart outflow is diminished or reduced such as by a collapse, kink, or restriction in the heart chambers or in the veins or arteries, when the heart goes into arrhythmia or malfunctions in any way during the operation, or when the heart is intentionally stopped such as by the application of cardioplegia to perform procedures such as valve surgery, internal surgery or other reason. This system is also desirable in any heart surgery procedure, even for anterior vessel bypass, when lifting or manipulating of the heart is not anticipated. This applies to both open chest and minimally invasive procedures.

By having this system in place before cardiac surgery begins, the present invention thus assures that the patient will at all times during the surgery have adequate pulmonary blood flow through the lungs and/or circulatory blood flow throughout the body. More importantly, it will avoid the necessity of being placed on a CPB machine in the event of an unexpected failure of the beating heart to sustain adequate pulmonary or circulatory blood flow during beating heart surgery. This allows the heart to continue to beat and provide pulmonary and circulatory blood flow to the extent it is capable, until there is a cardiac output compromise (such as by collapse, kink, arrhythmia or arrest, etc.) which decreases or stops the blood flow output by the heart. When that occurs, the pump(s) in either or both sides of the heart may be engaged to augment and/or replace the blood flow produced by the heart such that the patient's pulmonary and/or circulatory blood flows are maintained at sufficient levels to sustain them during the surgery. By having this system in place at the beginning of the beating heart surgery, even for anterior vessel surgery when no need is anticipated, it can merely be engaged or turned on to provide pump assisted blood flow if needed on an unexpected or emergency basis, thus assuring that emergency CPB procedures are avoided. Thus, this system assures that the patient's lungs are utilized for oxygenation of the blood during the entire surgical procedure, even if an unexpected compromise in blood flow from the beating heart occurs.

In one embodiment, the pump and cannula system is provided wherein the cannula portion is adapted for insertion through at least the pulmonary valve and a sufficient length into the pulmonary artery to provide a protected blood flow path within one or more of the right atrium, right ventricle, and pulmonary artery and the pump may be selectively operated to maintain at least a partial blood flow therethrough during beating heart surgery. Access for insertion of the cannula portion can be through the vena cava, e.g., from a femoral vein incision, through an incision in the wall of the vena cava or in the wall of the right atrium. If the cannula is not inserted through the tricuspid valve, but only through the pulmonary valve and into the pulmonary artery, access could be through an incision in the wall of the right ventricle or reverse access can be used by entering through an incision in the wall of the pulmonary artery. Separate cannulas can be employed, i.e., one introduced through the right atrium and through the tricuspid valve but ending in the right ventricle, and a second introduced by any desired access and beginning in the right ventricle and extending through the pulmonary valve and a desired length, according to this invention, into the pulmonary artery. The pump portion of the system is adapted for intake of blood upstream of the pulmonary valve or upstream of the tricuspid valve and output of blood into the right ventricle or into the pulmonary artery during beating heart surgery. The pump system may be integral with the above cannula or cannulas, particularly in a concentric double wall cannula configuration, or can comprise pump cannulas separate from and in addition to the above cannulas which protect the right side from collapse.

In another embodiment, a separate pump and cannula system may be provided for the left side wherein the cannula portion is adapted for insertion through at least the aortic valve and a sufficient length into the aorta to provide a protected blood flow path within one or more of the pulmonary vein, left atrium, left ventricle, and aorta, and the pump may be selectively operated to maintain at least partial blood flow therethrough during beating heart surgery. As indicated above for the right side, access for the left side cannula or cannulas can be from any desired upstream or downstream incision. One or two cannulas may be employed for preventing collapse of the left side. The pump portion of the system, which may have its separate cannulas, is adapted for intake of blood upstream of the aortic valve or the bicuspid valve and output of blood into the left ventricle or the aorta during beating heart surgery.

The pump and cannula systems of the present invention may be used in either the right side system or the left side system or both depending on the particular patient or procedure. Whether the cannula for pump output extends into the pulmonary artery/aorta or extends only into the respective ventricle will similarly depend on the requirements for a particular patient or procedure. In some instances, the beating heart blood flow may be impeded due to partial compression, wrinkling or other distortion of the ventricle muscle. Although the muscle is working, it is unable to both fill the ventricle with blood and expel or pump the blood in sufficient quantity. The pump system of this invention can be used by positioning the pump cannula output end in the ventricle to fill or preload the ventricle with blood, so the heart muscle can then pump or expel the blood from the ventricle, even though the muscle is not in its normal shape or position. In this aspect of the invention, beating heart blood flow can be maintained during surgery without the necessity of the cannula extending through the pulmonary/aortic valve. The heart may be stopped by short acting drugs that which stop the heart for a short period of time, or by electrical means affecting the electrical conduction of the heart or neurological systems or by use of electrical current to paralyze the nerves responsible for heart beating. While the heart is stopped, the pump(s) will deliver 100% of the necessary pulmonary blood flow to and from the lungs and/or 100% of the necessary circulatory blood flow to and from the body without any assistance from the heart. In the event the heart is stopped, and particularly when the heart is opened (such as for valve surgery), it is preferred to provide a seal by balloon sheath cannula, clamp or otherwise to isolate the heart, or at least one side of the heart, at the intake cannula and output cannula so that the pumped blood is directed from the vein to the artery without leakage or backflow into the heart during the surgery. This will enhance the pulmonary and/or circulatory blood flow provided by the pump in the pump and cannula system.

The pump and cannula systems disclosed herein for use in heart surgery according to the present invention preferably have a priming volume less than about 1,000 ml, and more preferably less than about 100 ml. Optimally, each individual pump/cannula unit will have a priming volume less than about 50 ml, preferably less than about 30 ml and more preferably less than about 10 ml. In one preferred embodiment, the pump and cannula system comprises concentric intake and output conduits (forming a generally coaxial dual cannula assembly), adapted for insertion into a single incision. In another preferred embodiment of this aspect of the invention, the pump and cannula system comprise an intake cannula for insertion in the upstream vessel or heart chamber and an output cannula for insertion downstream into the pulmonary artery or the aorta. In a further preferred embodiment of this aspect, the pump and cannula system may comprise a miniaturized pump having a sterile drive motor suitable for placement of the pump including the drive motor close to the chest and in the sterile zone, or preferably within the chest cavity itself during the heart surgery. In a further preferred embodiment of this aspect, a reverse flow pump and coaxial cannula combination may be employed having a minimum priming volume, although it is to be understood that any number of conventional pumping systems may be employed without departing from the scope of the present invention, including but not limited to a centrifugal pump, a cable driven axial flow pump, and a roller pump.

In another aspect, this invention provides a cannula system for protecting selected portions or all of the right side from collapse or kinking during beating heart surgery, an optional cannula system for protecting selected portions or all of the left side from collapse or kinking, and optional pump systems for use with the right and/or left side protection cannulas, if needed to supplement or augment the blood flow provided by the beating heart. In some patients all that may be required is the protection cannula or cannulas in the right side to allow the beating heart to maintain sufficient pulmonary and circulatory blood flow during the beating heart bypass surgery and it may not be necessary to use the pump system to provide supplemental pulmonary blood flow and may not be necessary to protect the left side or to provide supplemental circulatory blood flow. For such patients, this invention enables beating heart bypass surgery without artificial pumping of the blood and with minimum invasive apparatus. In some patients, beating heart bypass surgery can be started or attempted with only right side protection cannula(s) in place, then right side supplemental pumping of pulmonary blood flow added during the bypass surgery (or after the surgery) by separately inserting the pump system according to this invention. Likewise, left side protection cannula(s) and/or left side supplemental pumping of arterial blood can be added as needed during (or after) the bypass surgery by insertion of the cannula(s) and/or pump systems according to this invention. Thus, this invention provides optional incremental apparatus that may be selected by the surgeon and used only according to particular patient needs in order to minimize the invasiveness of the bypass surgery procedure.

The second system of the present invention may also take a variety of different forms. Generally speaking, the second system involves establishing a protected blood flow path within portions of the heart such that the heart's natural pumping activity will maintain at least partial blood flow therethrough during beating heart surgery to ensure sufficient pulmonary and/or circulatory blood flow, thereby avoiding the need for CPB. Establishing a protected blood flow path may be accomplished through the placement of one or more conduits, such as cannulas and/or stents, in certain heart chambers, in the venous and/or arterial vessels proximate to the heart, and/or in those areas or zones where collapse or kinking during manipulation of the beating heart during surgery is likely to occur and thus compromise the desired pulmonary and/or circulatory blood flow. Such conduits are placed as desired before or during surgery to allow the beating heart to provide at least a minimum but sufficient pulmonary and circulatory blood flow during surgery. Even when kinking, restriction or collapse of a vein, artery or heart chamber occurs during surgery, the beating heart is still provided a protected passageway equal to the inside diameter of the conduit through which the heart can maintain at least partial blood flow. In this system, no pump is provided and the blood flow is provided solely by the beating heart. By protecting the blood path from restriction or collapse, this system assures the output of the beating heart is available at all times during the surgery to sustain the patient during surgery with sufficient pulmonary and circulatory blood flow. As is apparent, this system is adapted for use exclusively in beating heart procedures. Conduits according to the invention may be provided with or without check valves and the placement thereof are described in detail below.

In one aspect, the second system involves a valved cannula for beating heart surgery having an outside diameter adapted for positioning in the right ventricle through the pulmonary valve and in the pulmonary artery, having a blood inlet in the ventricle portion, a blood outlet in the artery portion, a one-way valve or check valve between the inlet and outlet adapted to allow blood flow substantially only in one direction from the inlet toward the outlet. A positioning lead may be attached to the cannula for holding the cannula in proper position. This pulmonary valve cannula is adapted to receive blood through the inlet from the right ventricle when the right ventricle contracts and expel the blood through the outlet in the pulmonary artery. The one-way valve is adapted to prevent significant back flow of blood through the cannula back into the right ventricle. The cannula may be adapted and sized to allow blood to flow between the pulmonary valve and the external surface of the cannula when the right ventricle contracts and to allow the pulmonary valve to substantially seal to the external surface of the cannula and prevent significant back flow of blood around the cannula back into the right ventricle, when the right ventricle expands. The portion of the cannula contacting the pulmonary valve can be a different outside diameter than the ventricle portion or the artery portion of the cannula, or both. It may be desirable in some patients to have the outside diameter of the cannula at the pulmonary valve contact portion smaller to allow the maximum beating heart blood flow around the outside of the cannula when the pulmonary valve opens. In other patients it may be desirable to have a larger diameter to maximize the beating heart blood flow through the cannula as opposed to around the cannula. The inlet and outlet can be conventional blood cannula configurations and/or can comprise orifices, slits or other openings at desired locations and intervals along portions of the length of the cannula. The ends or openings can comprise baskets, cages or other guards to prevent suction of heart tissue or blood vessel wall into the cannula. The internal valve in the cannula can be any suitable one-way or check valve, such as a flap valve, slide valve, spring loaded circular valve or ball valve, membrane valve, duck bill valve or other design and can be any material appropriate for a blood flow valve. The positioning lead can be attached to the cannula in any desired way and any desired location and adapted for holding the cannula in position during use. The lead can also be useful in inserting and guiding the cannula through the appropriate vessel incision into proper position. The cannula can be inserted with a guide wire/balloon arrangement from an upstream incision.

In another aspect, the second system involves a valved cannula for beating heart surgery having an outside diameter adapted for positioning in the right atrium through the tricuspid valve and in the right ventricle, having a blood inlet in the atrium portion, a blood outlet in the ventricle portion, a one-way valve or check valve between the inlet and outlet adapted to allow blood flow substantially only in one direction from the inlet toward the outlet. A positioning lead may be attached to the cannula for holding the cannula in proper position. This tricuspid valve cannula is adapted to receive blood through the inlet from the right atrium and expel the blood through the outlet in the right ventricle when the right ventricle expands. The one-way valve is adapted to prevent significant back flow of blood through the cannula back into the right atrium when the right ventricle contracts. The cannula is preferably adapted and sized to allow blood to flow between the tricuspid valve and the external surface of the cannula when the right ventricle expands and to allow the tricuspid valve to substantially seal to the external surface of the cannula and prevent significant back flow of blood around the cannula back into the right ventricle when the right ventricle contracts. The portion of the cannula contacting the tricuspid valve can be a different outside diameter than the atrium portion or the ventricle portion of the cannula, or both. It may be desirable in some patients to have the outside diameter of the cannula at the tricuspid valve contact portion smaller to allow the maximum beating heart blood flow around the outside of the cannula when the tricuspid valve opens. In other patients it may be desirable to have a larger diameter to maximize the beating heart blood flow through the cannula as opposed to around the cannula. The inlet and outlet can be conventional blood cannula configuration and/or can comprise orifices, slits or other openings at desired locations and intervals along portions of the length of the cannula basket or cage to prevent heart tissue suction. The ends or openings can comprise baskets, cages or other guards to prevent suction of heart tissue or blood vessel wall into the cannula. The internal valve in the cannula can be any suitable one-way or check valve, such as a flap valve, slide valve, spring loaded circular valve or ball valve, membrane valve, duck bill valve or other design and can be any material appropriate to a blood flow valve. The positioning lead can be attached to the cannula in any desired way and any desired location and adapted for holding the cannula in position during use. The lead can also be useful in inserting and guiding the cannula through the appropriate vessel incision into proper position. The cannula can be inserted with a guide wire/balloon arrangement from an upstream incision.

In another aspect, the above pulmonary valve cannula and the above tricuspid valve cannula may be combined or formed as a single cannula adapted to the position through both the tricuspid and pulmonary valves with the respective check valves, inlets and outlets properly positioned according to the functions set forth above for each. The advantages of this single cannula configuration include single incision, single guide wire, and single positioning lead.

In another aspect, the second system may comprise a separately adapted stent to prevent collapse or kinking of the pulmonary artery to maintain blood flow through the pulmonary artery and/or through the stent during beating heart bypass surgery. When the beating heart is lifted and manipulated for surgical access to the posterior or lateral blood vessels, the pulmonary artery tends to fold or kink and restrict or stop the beating heart blood flow. A clamp or stabilizer can be applied to the external surface of the heart to take in the slack from the heart muscle and allow the muscle to function and to generate the contraction to eject blood even if the heart muscle is wrinkled. As used herein, the pulmonary artery "kink zone" is the portion of the pulmonary artery between the heart and the lungs where the artery tends to fold, kink or restrict when the beating heart is lifted or manipulated for surgical access to the lateral or posterior heart vessels. This kink zone is in the portion of the pulmonary artery within about 15 cm from the heart and usually within about 10 cm. In this aspect of the invention, the pulmonary artery stent is adapted to have diameter and length appropriate to extend the length of the kink zone and an appropriate distance on either side of the kink zone to assure full protection of the pulmonary artery during a beating heart surgical procedure. The pulmonary artery stent may include a handle for inserting and withdrawing the stent through an appropriate incision. Typically, the stent will further comprise a guide wire/balloon for placement of the stent in the proper position in the pulmonary artery. In some patients, the pulmonary artery stent may be all that is required to protect the left side during a particular beating heart surgical procedure. In other instances, the beating heart surgery may require only the pulmonary artery stent and the above tricuspid valve cannula. In other instances, the use of a pump and cannula system described above may be needed to supplement or augment the right side flow of blood produced by the beating heart during bypass surgery.

This invention further provides the above stent adapted for positioning in other portions of the right side to prevent collapse or restriction in a similar "kink zone" in the vena cava veins, right atrium or right ventricle and to maintain pulmonary blood flow through the right side while the heart is displaced and manipulated during beating heart bypass surgery. As is apparent, the above stent may also be adapted for positioning in the aorta, pulmonary veins, left atrium and/or left ventricle to maintain aortic beating heart blood flow during beating heart bypass surgery.

Both systems of the present invention may be used in conjunction with procedures involving collapsing one lung and/or partially reducing the size of the beating heart to provide additional space in the chest cavity in which the surgeon can work. In this regard, it is noted that one lung is normally sufficient to sustain the patient during surgery. In some procedures the surgeon prefers to collapse one lung to provide additional space inside the chest cavity in which to work. Both systems of the present invention can accommodate such a procedure while sustaining the patient on one lung throughout the surgery and avoiding a CPB machine. Likewise, it is sometimes desired by the surgeon to shrink down the heart by evacuating blood from one or more chambers of the heart, also to provide additional space within the chest cavity in which to work. The pump and cannula system of the present invention accommodates such a procedure because it can sustain adequate pulmonary and circulatory blood flow throughout the surgical procedure.

As is apparent, this invention enables the use of various combinations of the above aspects of this invention to meet the requirements of a particular patient for the successful performance of beating heart surgery while assuring that the patient's lungs (or lung) provides the oxygenated blood to sustain the patient through the surgery and that a CPB machine and procedure is avoided. Selective use of the above stents, cannulas and/or pump and cannula systems in their various configurations results in minimum invasiveness and minimum contact of the blood with apparatus in or outside the body during beating heart bypass surgery. Thus, this invention enables all beating heart surgical procedures without the use of a CPB machine by providing methods and apparatus systems ranging from one or more stents placed to prevent restriction of blood flow produced by the beating heart to pump and cannula systems placed through or around the entire right side and/or through or around the entire left side to both protect the beating heart blood flow and to augment, supplement or, when necessary, temporarily replace the beating heart blood flow during the surgery. This invention thus enables various heart surgery procedures to be performed without the use of CPB machines by maintaining sufficient pulmonary blood flow through the patient's lungs (or lung) and sufficient circulatory blood flow through the patient's body to sustain the patient during the surgery.

BRIEF DESCRIPTION OF THE DRAWINGS

FIGS. 16A–16D are cross-sectional views of the intravascular dual cannula arrangement shown in FIG. 15 taken along lines 16—16 illustrating exemplary manners of slideably coupling the cannulas to one another;

FIG. 17 is a side view of another intravascular dual cannula arrangement for providing right heart support during beating heart surgery according to the present invention;

FIGS. 18A—18B are cross-sectional views of the intravascular dual cannula arrangement shown in FIG. 17 taken along lines 18—18 illustrating exemplary manners of slideably coupling the cannulas to one another;

DETAILED DESCRIPTION OF THE INVENTION

Figure 1:
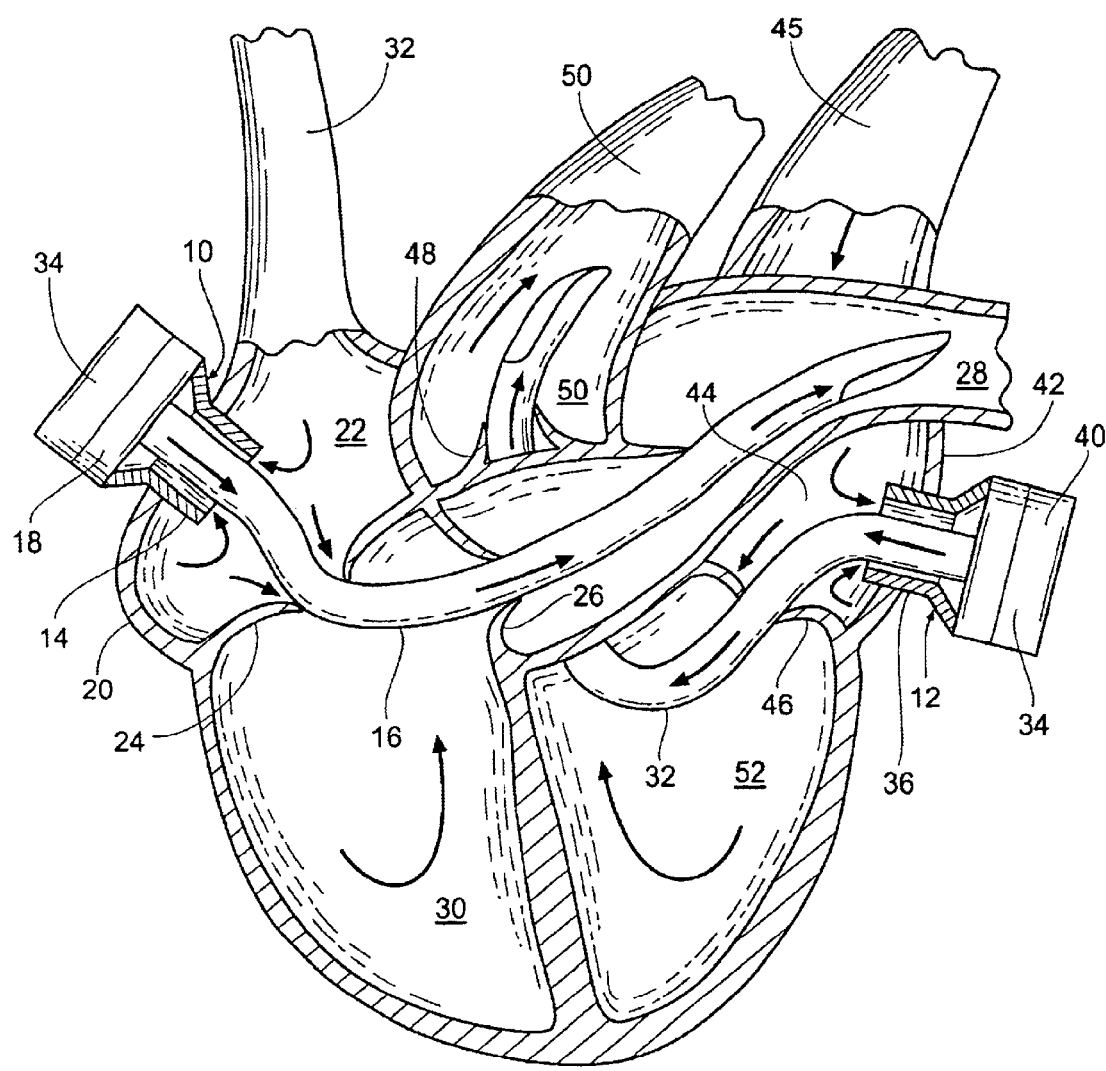
FIG. 1 is a sectional schematic view showing first and second pump and cannula systems within a heart for providing right and/or left heart support during beating heart surgery according to the present invention.

The present invention addresses the need to eliminate the use of CBP or other external blood oxygenation devices or procedures in beating heart surgery. The present invention accomplishes this by providing a method of performing beating heart surgery involving the step of maintaining at least partial blood flow through a protected blood flow path within the right and/or left side of the heart during surgery. Two basic systems are disclosed herein for effectuating the methods of the present invention. These systems can be employed alone or in combination depending upon the cardiac procedure to be undertaken. In both systems, the protected blood flow path is established by positioning one or more conduits within at least a portion of the right and/or left sides(s) of the heart. In the first system, at least partial blood flow is maintained through the protected blood flow path by the pumping action of a blood pump communicatively coupled to the conduit. In the second system, at least partial blood flow is maintained through the protected blood flow path by the pumping action of the beating heart itself. The following discussion will initially address the multitude of pump and cannula systems falling under the first system, followed by a discussion of the multitude of cannula and/or stent embodiments falling under the second system.

The first main system for carrying out the method of performing beating heart surgery according to the present invention can take any of a variety of forms. The common denominator between all embodiments, however, is the combined use of at least one cannula positioned within at least a portion of the right and/or left heart to establish a protected blood flow path, and a pump to maintain at least partial blood flow through the protected blood flow path during beating heart surgery. It enables safe heart surgery on anterior lateral and posterior blood vessels, in either beating heart or still heart procedures, without the necessity of using CPB. The pump and cannula systems disclosed herein can provide right heart support during beating heart surgery by pumping blood through or across the right side of the heart to augment or supplement pulmonary blood flow produced by the beating heart during surgery. If the heart temporarily collapses or lapses into arrest or disrhythmia during surgery, the supplemental pulmonary blood flow provided by the pump system of this invention eliminates the necessity of the use of CPB. During beating heart surgery, a temporary collapse or disrhythmia can be corrected to restore the beating of the heart, during which time the pump system of this invention will deliver sufficient supplemental pulmonary blood flow through the lungs to satisfy the patient requirements. Similarly, the pump system of this invention for the left side of the heart can likewise provide sufficient supplemental arterial flow of blood to satisfy the patient requirement until any compromise condition, such as heart collapse or disrhythmia, is corrected during beating heart surgery, thereby avoiding the need for CPB. By way of example only, the pump and cannula systems described below are useful in a variety of cardiac applications, including but not limited to procedures involving coronary artery bypass graft (CABG). In addition to avoiding the need for CPB, the pump and cannula systems of the present invention are also advantageous in that, by augmenting or replacing the pumping function of the right and/or left ventricle, the heart naturally decompresses (due to the reduced blood volume) which allows a greater degree of freedom to rotate and manipulate the heart for better access to target bypass vessels. This is particularly important in endoscopic surgery. While the pump and cannula systems disclosed herein are discussed primarily with respect to their usefulness in providing right and/or left heart support during beating heart surgery, it is to be readily understood that these pump and cannula systems also enable still heart surgery, such as valve or other internal heart repair, without the use of CPB.

In a preferred embodiment of this invention, the pump and cannula system utilizes a dual lumen cannula assembly having an inner cannula extending generally concentrically or coaxially through an outer cannula The proximal ends of the inner and outer cannulas are communicatively coupled to a pumping arrangement, and the distal end of the inner cannula extends, in use, past the distal end of the outer cannula. A first flow path is thus established within the inner cannula, while a second flow path is established within an annular space extending between the exterior surface of the inner cannula and the interior surface of the outer cannula. In this system, the concentric double cannula can be introduced into the heart through a single incision and positioned such that the distal end of the outer cannula is in a first location and the distal end of the inner cannula is in a second location. The pumping arrangement may then be employed to withdraw blood from one of the locations and reroute the blood to the other location. This system is advantageous in that it provides the ability to unload portions of the heart in an effort to stabilize the heart during beating heart surgery. It also advantageously provides the ability to establish a protected blood path within the right and/or left heart through which blood may be selectively pumped to maintain adequate pulmonary and/or circulatory blood flow during beating heart surgery.

FIG. 1 illustrates exemplary dual lumen cannula and pump systems according to the first system for carrying out the methods of the present invention. A pump and cannula system 10 is provided for supporting the right heart during cardiac surgery. An optional pump and cannula system 12 is provided for supporting the left heart during cardiac surgery. Pump and cannula systems 10, 12 are of the type shown and described in co-pending and commonly-assigned U.S. patent application Ser. No. 09/231,320, filed Jan. 13, 1999, and U.S. patent application Ser. No. 09/079,836, filed May 15, 1998, the contents of which are incorporated herein by reference.

The pump and cannula system 10 for right heart support includes an outer cannula 14, an inner cannula 16, and (by way of example only) a reverse flow pump 18 communicatively coupled to the proximal ends of the inner cannula 16 and outer cannula 14. The outer cannula 14 extends through the wall 20 of the right atrium 22. The inner cannula 16 is disposed generally co-axially within the outer cannula 14 and is preferably moveably displaceable relative to the outer cannula 14 such that the distal end of the inner cannula 16 may be selectively positioned to a predetermined location within the heart. In the embodiment shown, the distal end of the inner cannula 16 is positioned such that it extends, in use, past the distal end of the outer cannula 14, through the tricuspid valve 24, the pulmonary valve 26, and a sufficient length and distance into the pulmonary artery 28. The reverse flow pump 18 may be selectively operated (i.e. automatically or on-demand) to withdraw blood from the right atrium 22, through the flow path defined between the outer cannula 14 and the exterior of the inner cannula 16, and through the flow path defined within the inner cannula 16 for deposit into the pulmonary artery 28. In this fashion, blood entering the right atrium 22 may be selectively rerouted past the right ventricle 30 in an effort to supplement or replace the pumping action of the right ventricle 30 and overcome conditions where the cardiac output may become compromised during beating heart surgery. The negative pressure that develops within the right atrium 22 due to the pump 18 also advantageously draws blood through or past areas of occlusion, collapse or kinking in the superior vena cava 32 and the inferior vena cava (not shown).

The pump and cannula system 10 for right heart support enables the heart to continue pumping blood in its normal fashion to provide pulmonary blood flow around cannula 14, to the extent that the heart is capable, during the lifting and manipulation of the heart during surgery. The cannula and pump system 10 assures a supplemented or augmented flow of blood to the pulmonary artery 28, even in the event of compromised cardiac output, such as by disrhythmia or other interruption of pulmonary blood flow by the beating heart. Under normal circumstances, and at most times during the beating heart surgery, the internal support provided by cannula 16 will prevent the collapse of the right side of the heart and enable the heart to continue pumping at least a portion of its normal blood output into pulmonary artery 28. The combined flow of the blood flow produced by the beating heart and the blood flow produced by pump 18 and transported through the inner cannula 16 is at all times sufficient to sustain adequate pulmonary blood flow to sustain the patient during surgery. In the event of a disrhythmia, the pump 18 can be increased in output to compensate until the disrhythmia is corrected. The pump and cannula system 10 can thus overcome any compromise in right heart function or output during beating heart surgery (such as collapse or kinking that may occur in the vena cava 32, right atrium 22, right ventricle 30, and/or pulmonary artery 28 when the heart is lifted or manipulated) and thus avoid the need for CPB.

The cannulas 14, 16 of the right heart support system 10 are preferably inserted through a single incision in the wall 20 of right atrium 22 as illustrated, although it is contemplated to insert them through an incision in the vena cava 32 or right ventricle 30. The outer cannula 14 is preferably sealed within the incision formed in the wall of right atrium 22 through the use of a purse-string suture, as well known in the art, or any other suitable sealing mechanisms. The outer conduit 14 provides the annular space between outer conduit 14 and inner conduit 16 for the inflow of blood to the pump 18, which is driven by a motor 34. The step of inserting the inner cannula 16 through tricuspid valve 24, pulmonary valve 26 and into pulmonary artery 28 may be accomplished in any conventional method, such as the optional use of a balloon or guidewire. The length into which the inner cannula 16 extends past the pulmonary valve 26 into pulmonary artery 28 will depend on the beating heart surgical procedure being performed and on other factors. In general, the inner cannula 16 should extend through and past an area defined as the "kink zone," which will vary in size and location depending on condition of the patient, the surgical procedure performed and the extent of movement and manipulation of the heart during surgery. The kink zone will frequently extend up to the point where the pulmonary artery is not moved during surgery. It is generally expected that the inner cannula 16 will need to extend up to about 15 cm beyond pulmonary valve 26 and into pulmonary artery 28. Such a length is generally sufficient to prevent kinking or collapsing of pulmonary artery 28 during the positioning of the heart for beating heart bypass surgery. Preferably, the length beyond the pulmonary valve 26 will generally be up to about 10 cm, or preferably up to about 7 cm, or about 4 cm but may be as little as about 1 cm depending on the kind and size of cannula used.

The pump and cannula system 12 for left heart support functions in generally the same manner as the pump and cannula system 10 for right heart support described above. The pump and cannula system 12 for left heart support includes an outer cannula 36, an inner cannula 38, and (by way of example only) a reverse flow pump 40 communicatively coupled to the proximal ends of the outer cannula 36 and inner cannula 38. The outer cannula 36 extends through the wall 42 of the left atrium 44. The inner cannula 38 is disposed generally co-axially within the outer cannula 36 and is preferably moveably displaceable relative to the outer cannula 36 such that the distal end of the inner cannula 38 may be selectively positioned within the heart. As with the right side, concentric cannulas 36, 38 are inserted into a single incision in the wall of the left atrium 44 and preferably sealed with the wall at the incision through any well known method, such as by a purse-string suture. In the embodiment shown, the distal end of the inner cannula 38 is positioned such that it extends, in use, past the distal end of the outer cannula 36, through the bicuspid valve 46, through the aortic valve 48, and a sufficient length into the aorta 50. The reverse flow pump 40 may be selectively operated (i.e. automatically or on-demand) to withdraw blood from the left atrium 44, through the flow path defined between the outer cannula 36 and the exterior of the inner cannula 38, and through the flow path defined within the inner cannula 38 for deposit into the aorta 50. This establishes a protected blood flow path within the left atrium 44, left ventricle 52, and aorta 50 such that, under the direction of the pump 40, the aortic or circulatory blood flow from the heart may be selectively augmented during beating heart surgery, thereby avoiding the need for CPB. The pump and cannula system 12 is thus capable of overcoming any compromise in left heart function or output during beating heart surgery, such as collapse or kinking that may occur in the left atrium 44, left ventricle 52, and/or aorta 50 when the heart is lifted or manipulated to provide surgical access to lateral or posterior heart vessels.

One advantage of the right and left heart support pump and cannula systems 10, 12 is that they allow the beating heart to continue to pump whatever blood it is capable of pumping under the conditions of the beating heart surgery. When the right and/or left side(s) of the heart is supported according to this invention to establish a protected blood flow path therein (thus preventing collapse, kinking, or occlusion of the right and/or left sides), the beating heart can provide substantial, if not full or sufficient, pulmonary and/or circulatory blood flow during the beating heart surgery. The pump and cannula system 10 can advantageously provide auxiliary or supplemental blood flow through the right side into the pulmonary artery 28 to assure that adequate pulmonary blood flow is maintained at all times during the surgery. The pump and cannula system 12 can advantageously provide auxiliary or supplemental blood flow through the left side of the heart into the aorta 50 to assure that adequate arterial circulatory blood flow is maintained at all times during the surgery. In an important aspect, the exemplary pump and cannula systems 10, 12 may be employed, alone or in combination, to effectuate the method of performing beating heart surgery according to the present invention and thus avoid the need for CPB in such cardiac procedures.

In the embodiment shown, pumps 18, 40 each comprise reverse flow pumps of the type disclosed in commonly assigned and co-pending U.S. application Ser. No. 08/933,566, filed Sep. 19, 1997, and PCT Application Ser. No. US97/18674, filed Oct. 14, 1997, now published as WO 99/02204, the disclosures of which are incorporated herein by reference. The pumps 18, 40 can be controlled to provide essentially no auxiliary or supplemental blood flow while the beating heart is providing adequate flow through the supported portion or portions of the right and/or left side(s), or to provide full supporting pulmonary and/or circulatory blood flow in the event the output flow of the beating heart decreases or stops. In a preferred embodiment, the pumps 18, 40 can be controlled by a controller in response to conventional parameters, such as oxygen level measured by conventional oximeters, blood pressure measured by conventional means, or other parameters desired to assure proper patient support during and after surgery, such as $CO_2$ level, flow rate, etc. As will be discussed in greater detail below, any of a variety of alternate pumps may be used other than the reverse flow pumps 18, 40 shown by way of example in FIG. 1.

An advantage of the foregoing systems is that the generally concentric cannulas, in combination with the reverse flow miniature pump, enables the installation of the pumps 18, 40 essentially adjacent to the incision where the double cannula 14, 16 is inserted into the right atrium wall 20 and where the double cannula 36, 38 is inserted into the left atrium wall 42. In this fashion, the priming volume of each pump and cannula system 10, 12 is minimized to less than about 1,000 ml, preferably less than about 200 ml, more preferably less than about 100 ml, and most preferably less than about 50 ml. In this context, "priming volume" refers to the volume of each pump and cannula system 10, 12 which is external of the patient and does not include the volume of the portions of the cannulas which are inserted into the patient and thus are immersed in the blood flow. It is especially preferred that the priming volume of each pump and cannula system 10, 12 be very small, typically less than 60 ml, preferably less than 30 ml, more preferably less than 20 ml, and most preferably less than about 10 ml. The advantages of the very small priming volume will be apparent to one skilled in the art.

Another advantage provided by the pump and cannula systems 10, 12 is that, by having the capability of placing the small priming volume pump (including its drive motor) adjacent to or very near the incision, the distance the blood must travel outside the body is minimized, thereby minimizing the amount of contact between the blood and the tubing, pump components and other apparatus. Among other things, this prevents the occurrence of hemolysis in the blood being transported. In addition, the pump can operate essentially at body temperature, thus eliminating the necessity of cooling or warming the blood, particularly because the blood is outside the body a very short distance and for a very short time. With this system, the entire pump and cannula system 10, 12 can be positioned near the chest cavity, within the chest cavity itself, near or adjacent to the heart, or can be positioned in a support cradle near or adjacent the heart to obtain the minimum possible pumped blood flow path. Other advantages will be apparent to one skilled in the art, including the fact that with the entire pump, drive motor and cannula system miniaturized and configured to be contained in the chest cavity or in a support cradle with the heart, this system eliminates the disadvantages of having numerous tubes, cables, etc., from the patient's chest cavity to external equipment. Even in the embodiment of the present invention where the pump and cannula system 10 is installed in or across the right side of the heart, and a separate pump and cannula system 12 is installed or across in the left side of the heart, the only lines extending from this system to external equipment is a single cable from each pump 18, 40 to an external power supply for providing power to these pumps. This single cable can contain electrical connection for supplying electrical power to the pump motor near the heart or can be a flexible drive cable to transmit power to the pump from a remote motor. Thus, the pump and cannula systems 10, 12 of this embodiment provides the surgeon improved surgical access to the heart and visibility of the heart by eliminating the CPB tubing and other associated cables and pumps which are conventionally used in bypass and other cardiac surgical procedures.

It is to be readily appreciated that the foregoing pump and cannula systems 10, 12, while advantageous over the prior art in many respects, are nonetheless presented by way of example and not limitation. That is to say, any number of alternate cannula configurations and designs may be employed without departing from the scope of the present invention, several of which will be discussed in detail below. Moreover, although shown above as a reverse flow pump, it is to be readily understood that any number of other known pumping arrangements can be employed with the dual cannula assemblies disclosed herein for the purpose of carrying out the methods of performing beating heart surgery according to the present invention.

Figure 2:
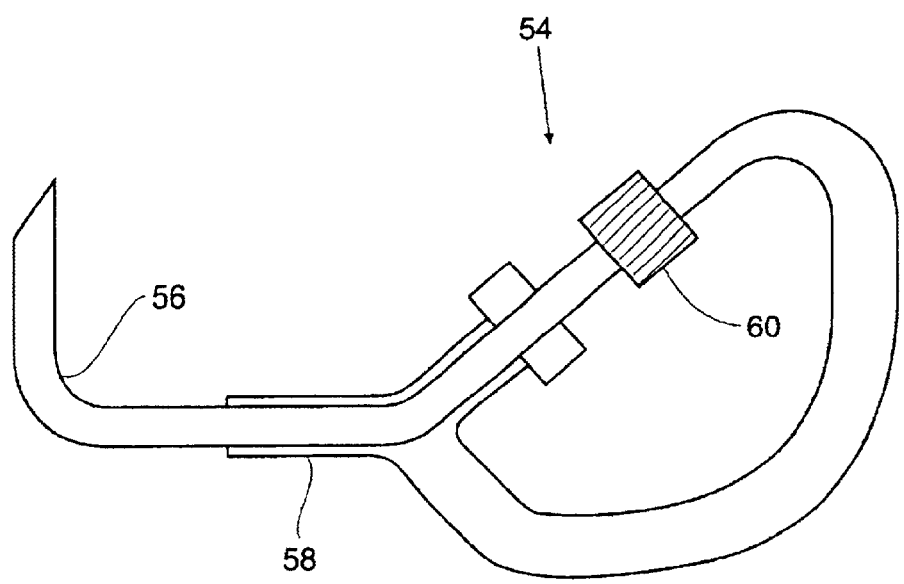
FIG. 2 is a schematic view illustrating an exemplary axial pumping arrangement for use with the pump and cannula systems of the present invention.
Figure 3:
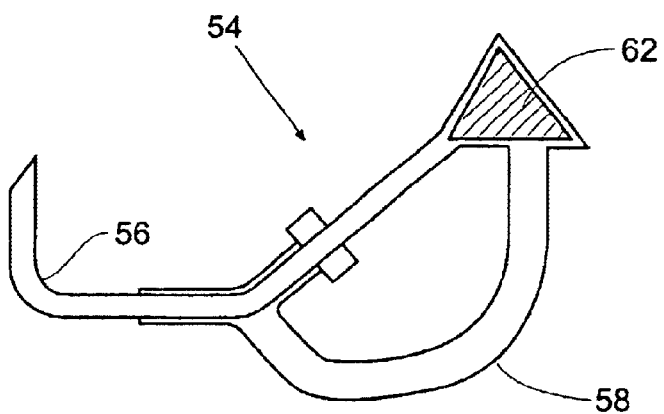
FIGS. 3 and 4 are schematic views illustrating exemplary centrifugal pumping arrangements for use with the pump and cannula systems of the present invention.
Figure 4:
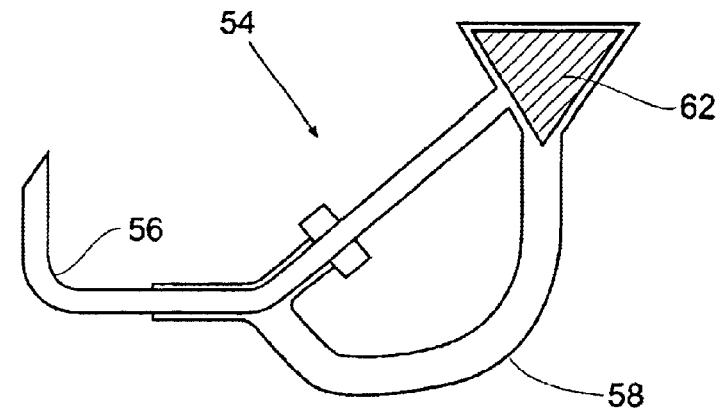
Figure 5:
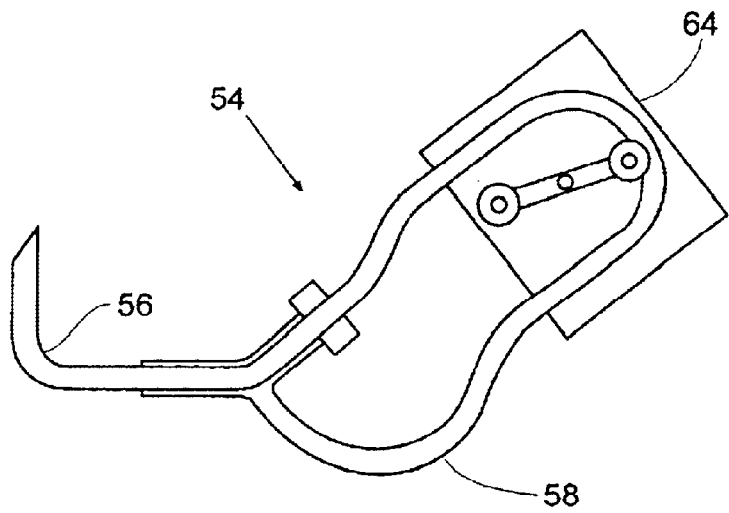
FIG. 5 is a schematic view illustrating an exemplary roller pumping arrangement for use with the pump and cannula systems of the present invention.

FIGS. 2–5 illustrate, by way of example only, several well known pumping arrangements that can be employed with the various dual cannula assemblies disclosed herein to carry out the methods of performing beating heart surgery according to the present invention. The dual cannula assemblies (to be described in detail below) are represented generally at 54 and include an inner cannula 56 extending generally concentrically within and out the distal end of an outer cannula 58. In each instance, a first flow path is defined within the interior of the inner cannula 56 and a second flow path is within the interior of the outer cannula 58 (including the annular space defined between the interior surface of the outer cannula 58 and the exterior surface of the inner cannula 56 extending to the distal end of the outer cannula 58). FIG. 2 illustrates an axial flow pump 60 that is communicatively coupled between the proximal ends of the inner cannula 56 and the outer cannula 58. The axial flow pump 60 may be selectively operated to withdraw blood through the first flow path and transport it out the second flow path or, alternately, the axial flow pump 60 may be reversed to withdraw blood through the second flow path and transport it out the first flow path. FIGS. 3–4 illustrate a centrifugal pump 62 communicatively coupled between the proximal ends of the inner cannula 56 and the outer cannula 58. In FIG. 3, the centrifugal pump 62 may be operated to withdraw blood through the first flow path and transport it out the second flow path. In FIG. 4, the centrifugal pump 62 is configured to withdraw blood through the second flow path and transport it out the first flow path. FIG. 5 illustrates a roller pump 64 communicatively coupled between the proximal ends of the inner cannula 56 and the outer cannula 58. The roller pump 64 may be selectively operated to withdraw blood through the first flow path and transport it out the second flow path or, alternately, the roller pump 64 may be reversed to withdraw blood through the second flow path and transport it out the first flow path. As will be appreciated, the foregoing pump and cannula systems 54 can be employed to provide right and/or left heart support by selectively positioning the distal ends of the inner and outer cannulas 56, 58 at predetermined, separate locations within the right and/or left side of the heart, and thereafter employing the pump to transport blood through the first and second flow paths.

The pump arrangements disclosed herein are preferably regulated through the use of a controller for each pump or a controller to control all pumps in a particular system. In one embodiment, pump speed and output may be controlled based on the measurement of a pressure transducer disposed at the arterial blood flow area to measure pulmonary artery blood pressure and aorta blood pressure. The central venous pressure can also be used separately or with the pulmonic and/or aortic pressure. The selected blood pressure measurement can provide the basis for a manual or automatic control of the individual and separate pump speeds and outputs. The desired or target pulmonary and aortic blood pressures can be determined by the surgical team for each patient depending on condition of the patient and surgical procedure being performed. The desired or target pressures may change or be different for different stages of the surgical procedure. In general, a desired pressure range is about 20–30 mmHg, although pressures as low as about 10–15 mmHg may be acceptable for limited periods of time. The controller can operate in response to one selected pressure or can operate in response to other parameters. It is further preferred that the controller and the control system incorporate other input data, in addition to arterial pressure, such as blood pressure elsewhere in the body, blood oxygen level, actual blood flow volume, blood $CO_2$ level, etc. A desired automatic control criteria is where a control loop for each pump is established whereby a target total blood flow is maintained by the sum of any beating heart blood flow output plus the pump flow output. Thus, the patient is assured of adequate pulmonary and circulatory blood flow throughout the surgery regardless of the output of the heart, without any CPB machine use. The pillmonary artery pressure and pulmonary blood flow rates will need to be adjusted accordingly when only one lung is being used during the surgery, and the aortic circulatory blood flow may also have to be adjusted in such mode of operation. The pump and cannula systems of this invention can provide 0–100% of the required blood flow to sustain the patient with the heart providing 100–0% of the blood flow. When the pump system is providing part of the blood flow in a beating heart procedure, the pump can provide about 10, 20, 30, 40, 50, is 60, 70, 80, or 90% of the total blood flow for the side of the heart in question with the beating heart providing the remainder of the blood flow needed to sustain the patient during the surgery.

As noted above, it is to be readily appreciated that any number of cannula configurations and designs (other than those represented in FIG. 1) may be employed without departing from the scope of the present invention. Following is a discussion of various dual lumen cannula embodiments that can be employed with any of the above-described pumping arrangements (including but not limited to reverse flow, axial flow, centrifugal flow, and roller types) to provide right and/or left heart support during cardiac surgery according to the present invention.

Figure 6:
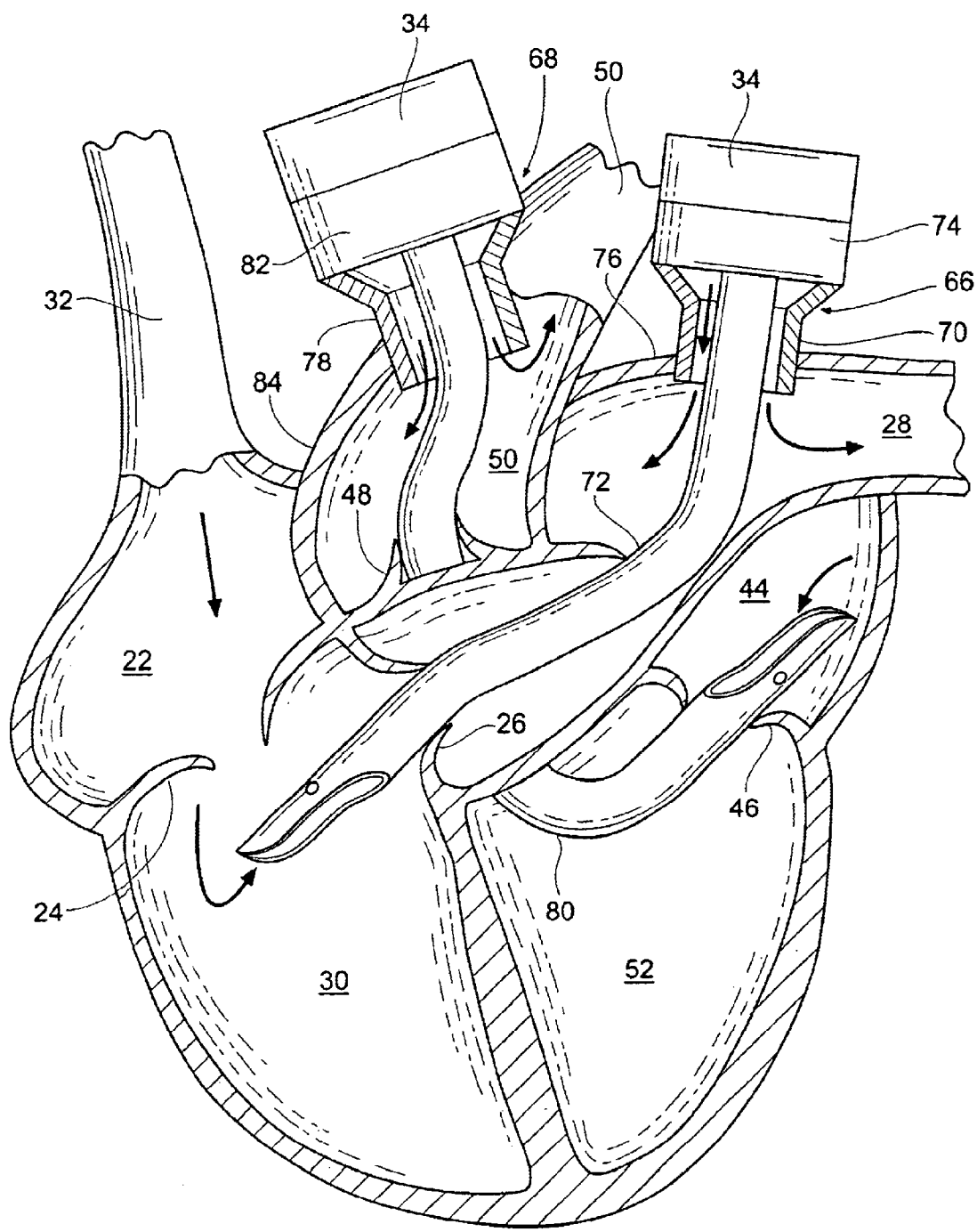
FIG. 6 is a sectional schematic view showing first and second pump and cannula systems within a heart for providing right and/or left heart support during beating heart surgery according to the present invention.

FIG. 6 illustrates additional dual lumen cannula and pump systems for carrying out the methods of the present invention. A pump and cannula system 66 is provided for supporting the right side of the heart during cardiac surgery. An optional pump and cannula system 68 may also be provided for supporting the left side of the heart during cardiac surgery. Pump and cannula systems 66, 68 are of the type shown and described in co-pending and commonly-assigned U.S. patent application Ser. No. 08/891,456, filed Jul. 11, 1997, and U.S. patent application Ser. No. 08/933,566, filed Sep. 19, 1997, the contents of which are both incorporated by reference herein.

The pump and cannula system 66 for right heart support includes an outer cannula 70, an inner cannula 72, and (by way of example only) a reverse flow pump 74 communicatively coupled to the proximal ends of the outer cannula 70 and inner cannula 72. The outer cannula 70 extends through the wall 76 of the pulmonary artery 28. The inner cannula 72 is disposed generally co-axially within the outer cannula 70 and is preferably moveably displaceable relative to the outer cannula 70 such that the distal end of the inner cannula 72 may be selectively positioned within the heart. In the embodiment shown, the distal end of the inner cannula 72 is positioned such that it extends, in use, past the distal end of the outer cannula 70, through the pulmonary artery 28, the pulmonary valve 26, and a sufficient length into the left ventricle 52. The reverse flow pump 74 may be the same type as those shown and described above with reference to FIG. 1. Pump 74 may be selectively operated (i.e. automatically or on-demand) to withdraw blood from the right ventricle 30, through the interior of the inner cannula 72, and through the flow path defined between the outer cannula 70 and the exterior of the inner cannula 72 for deposit into the pulmonary artery 28. Blood within the right ventricle 30 may thus be selectively transported through the pulmonary valve 26 and into the pulmonary artery 28 to supplement or replace the pumping action of the right ventricle and overcome conditions where the cardiac output may become compromised during beating heart surgery. In an important aspect, the suction or negative pressure that develops within the right ventricle 30 due to the pump 74 may serve to draw blood into the right atrium 22 and right ventricle 30 through or past areas of occlusion, collapse or kinking in the vena cava 32 (superior or inferior). The pump and cannula system 66 is thus capable of overcoming any compromise in right heart function or output during beating heart surgery, such as collapse or kinking that may occur in the vena cava 32, right atrium 22, right ventricle 30, and/or pulmonary artery 28 when the heart is lifted or manipulated to provide surgical access to lateral or posterior heart vessels.

The pump and cannula system 68 for left heart support includes an outer cannula 78, an inner cannula 80, and (by way of example only) a reverse flow pump 82 communicatively coupled to the proximal ends of the outer cannula 78 and inner cannula 80. The outer cannula 78 extends through the wall 84 of the aorta 50. The inner cannula 80 is disposed generally co-axially within the outer cannula 78 and is preferably moveably displaceable relative to the outer cannula 78 such that the distal end of the inner cannula 80 may be selectively positioned within the heart. In the embodiment shown, the distal end of the inner cannula 80 is positioned such that it extends, in use, past the distal end of the outer cannula 78, through the aorta 50, the aortic valve 48, the bicuspid valve 46, and into the left atrium 44 (or, although not shown, the left ventricle 52). The reverse flow pump 82 may be selectively operated (i.e. automatically or on-demand) to withdraw blood from the left atrium 44 through the flow path defined within the inner cannula 80, and through the flow path defined between the outer cannula 78 and the exterior of the inner cannula 80 for deposit into the aorta 50. This establishes a protected blood flow path within the left atrium 44, left ventricle 52, and aorta 50 such that, under the direction of the pump 82, the aortic or circulatory blood flow from the heart may be selectively augmented during beating heart surgery, thereby avoiding the need for CPB. The pump and cannula system 68 is thus capable of overcoming any compromise in left heart function or output during beating heart surgery, such as collapse or kinking that may occur in the left atrium 44, left ventricle 52, and/or aorta 50 when the heart is lifted or manipulated to provide surgical access to lateral or posterior heart vessels.

As will be appreciated, the pump and cannula systems 66, 68 of FIG. 6 share many of the same advantages and features of the pump and cannula systems 10, 12 shown and described in FIG. 1. For example, the outer cannulas 70, 78 of the pump and cannula systems 66, 68 can each be inserted through a single incision in the heart and sealed through the use of a purse-string suture, as well known in the art, or any other suitable sealing mechanisms. In each instance, the inner cannulas 72, 80 serve to establish a protected blood flow path within or through regions or zones where kinking or collapse may otherwise occur when the heart is lifted or manipulated during beating heart surgery. The pump and cannula systems 66, 68 allow the heart to continue pumping blood in its normal fashion to provide pulmonary and circulatory blood flow around the inner cannulas 72, 80 to the extent that the heart is capable during surgery. In the event of cardiac output compromise (such as decreased cardiac output due to collapse, kinking, or arrhythmia), the pump and cannula systems 66, 68 may be selectively employed (alone or in combination) to ensure a supplemented or augmented flow of blood to the pulmonary artery 28 and/or aorta 50.

Figure 7:
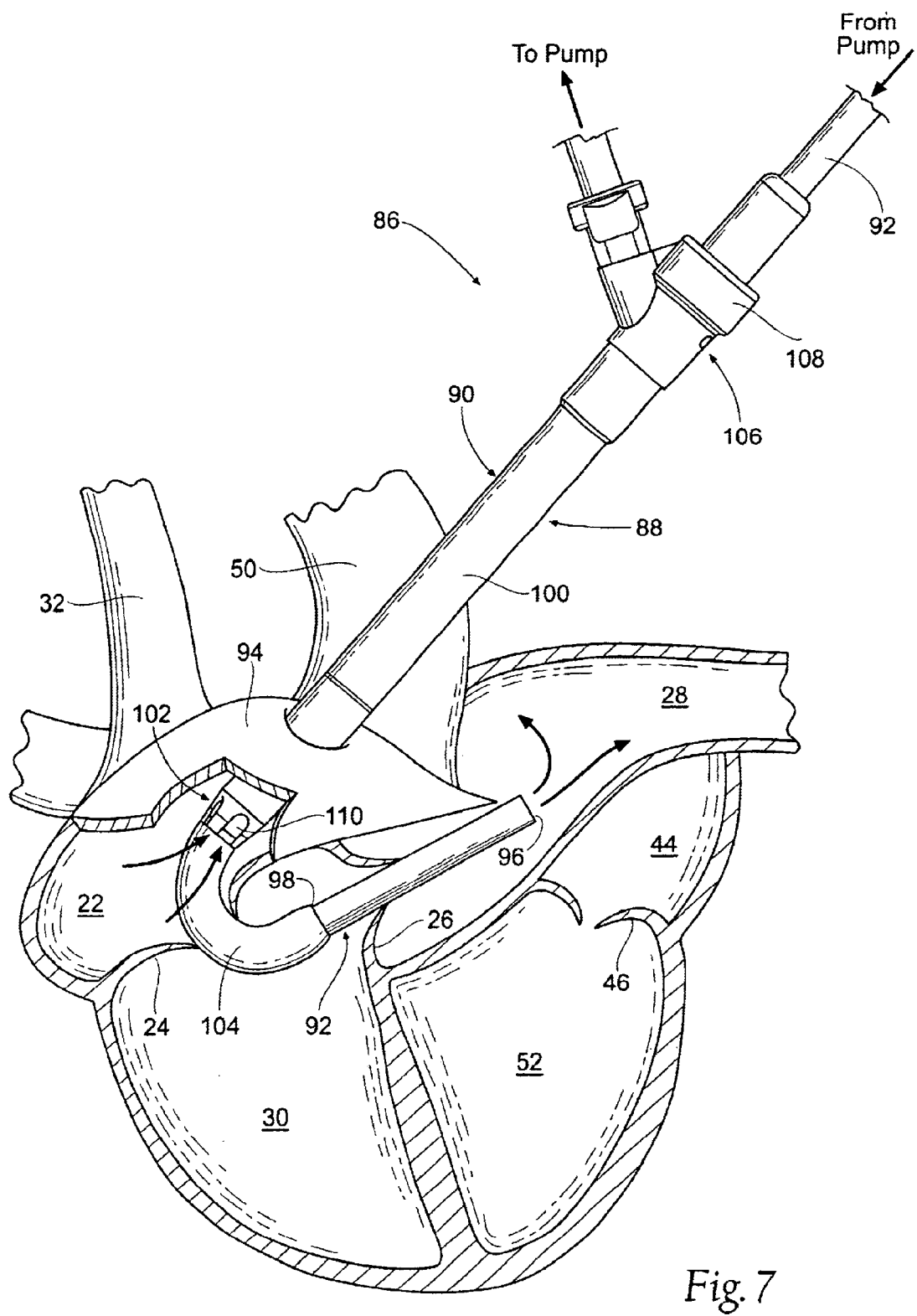
FIG. 7 is a sectional schematic view showing a dual cannula arrangement within a heart for providing right heart support during beating heart surgery according to the present invention.

FIG. 7 illustrates yet another dual lumen cannula and pump system for carrying out the methods of the present invention. In this embodiment, a pump and cannula system 86 comprises a dual cannula assembly 88 communicatively coupled to a pump (not shown) for supporting the right side of the heart during cardiac surgery. Pump and cannula system 86 is of the type shown and described in co-pending and commonly-assigned Int'l Patent App. Ser. No. PCT/US99/1366, filed Jun. 18, 1999, which claims priority to U.S. patent application Ser. No. 09/099,713, filed Jun. 19, 1998, and U.S. Provisional Patent App. Ser. No. 60/113,727, filed Dec. 23, 1998, the contents of which are incorporated by reference herein.

Figure 8:
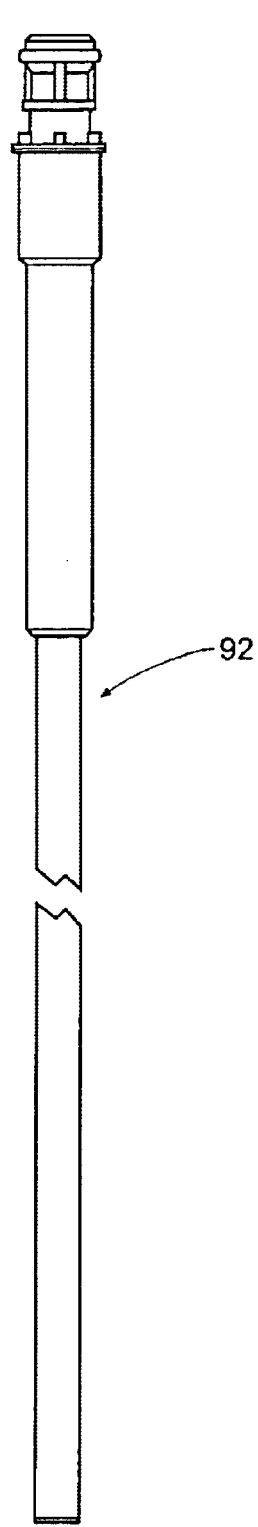
FIG. 8 is side view of an inner cannula of the dual cannula arrangement shown in FIG. 7.
Figure 9:
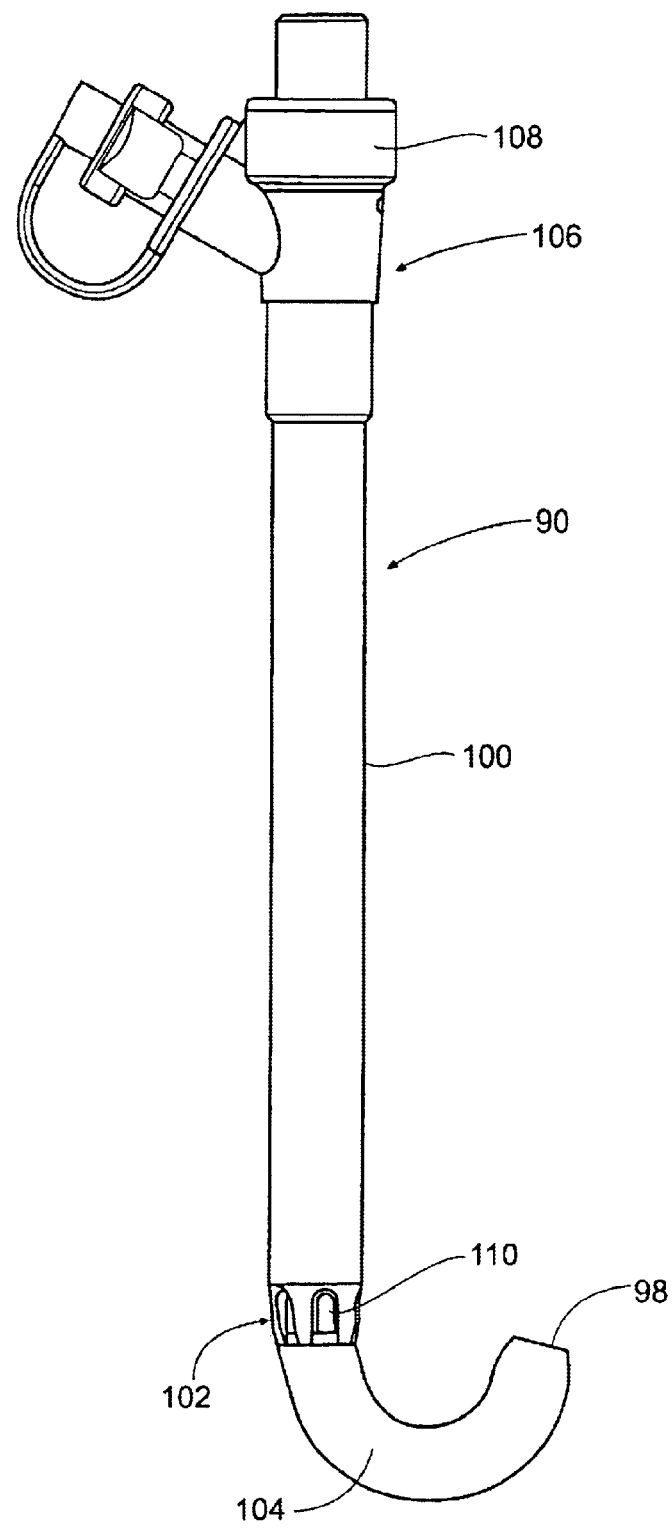
FIG. 9 is a side view of an outer cannula of the dual cannula arrangement shown in FIG. 7.

With combined reference to FIGS. 7–9, the dual cannula assembly 88 of this embodiment comprises an outer cannula 90 adapted to be introduced into the heart through the atrial appendage 94, and an inner cannula 92 disposed generally concentrically within the outer cannula 90 and having a distal end 96 adapted to extend, in use, past a distal end 98 of the outer cannula 90 and a sufficient length into the pulmonary artery 28. The outer cannula 90 is constructed by combining a main body 100, an inflow port 102, and a curved portion 104. A Y-connector 106 is coupled on the proximal end of the main body 100 and contains a hemostasis valve 108 which seals around inner cannula 92 and allows the inner cannula 92 to be slideably advanced through the outer cannula 90 while reducing the possibility of blood leakage or emboli forming within the patient's blood stream. The inflow port 102 is equipped with a plurality of fluid openings 110. In use, the outer cannula 90 is preferably introduced through a single incision in the heart such that the inflow port 102 is disposed within the right atrium 22. In an important aspect, the curved portion 104 is dimensioned such that, in use, its distal opening is positioned within the right ventricle 30 and directed generally at the pulmonary valve 26 to provide a guiding function for the placement of the inner cannula 92. Once the outer cannula 90 is positioned within the heart, the inner cannula 92 may be slideably advanced through the main body 100, the inflow port 102, and the curved portion 104 and guided into the pulmonary artery 28. The inner cannula 92 is thereafter preferably restricted from moving independent of the outer cannula 90, such as by clamping the inner cannula 92 proximal to the y-connector 106.

With the inner cannula 92 disposed generally concentrically within the outer cannula 90, a blood flow path to the pump is defined in the annular space between the exterior surface of the inner cannula 92 and the interior surface of the outer cannula 90, and a blood flow path from the pump is defined in the lumen of the inner cannula 92. The outer and inner cannulas 90, 92 therefore combine to establish a protected blood flow path within the right side of the heart. A pump (not shown) communicatively coupled to the proximal ends of the outer and inner cannulas 90, 92 is capable of maintaining at least partial blood flow within the protected blood flow path by selectively withdrawing blood from the right atrium 22 and transporting it through the tricuspid valve 24, the right ventricle 30, and pulmonary valve 26 for deposit into the pulmonary artery 28. In this fashion, the pump and cannula system 86 may be utilized to provide right heart support to overcome any of the above-identified compromise conditions in cardiac output that may occur during beating heart surgery.

The outer cannula 90 and inner cannula 92 may be formed of materials ranging from rigid to flexible, and in the preferred embodiment comprises a semi-rigid transparent material such as polyurethane, polyvinyl chloride (PVC) or other material. If needed, spiraling wire (not shown) may be molded into the walls of the outer and/or inner cannulas 90, 92 to provide additional structural support. As will be recognized, the wire adds rigidity and thus facilitates the handling and placement of the cannulas 90, 92. When imbedded in the outer cannula 90, the reinforcement wire reduces the possibility that it will collapse or become pinched shut so as to close off the flow of fluid to or from the patient, or impede or prevent the user from advancing the inner cannula 92 through the outer cannula 90. Other ways of reinforcing the cannulas 90, 92 are known in the art and will adapt equally well to the present invention. In addition, no reinforcement may be needed if the cannula material is sufficiently rigid or if sufficient fluid pressure is present within the cannula. The wire may be wound at varying pitch and density within the walls of the cannulas 90, 92 to create varying degrees of stiffness. For example, the curved portion 104 may thus be formed so that it is sufficiently stiff to provide the user with the ability to align distal tip 98 with the patient's pulmonary valve 26 so that the inner cannula 92 can be easily passed through the outer cannula 90 and directed into the pulmonary artery 28, and yet sufficiently flexible such that when the heart is rotated, the curved portion 104 will deflect or rotate with the heart. Although not shown, the outer and/or inner cannulas 90, 92 may be provided with any number of additional features. For example, the inner cannula 92 may be equipped with lumens disposed within the wall for inflating or deflating balloons disposed about the outer surface of the inner cannula 92 to assist in the placement of the inner cannula 92 within the pulmonary artery 28. Pressure transducers may also be provided within the walls of the outer and/or inner cannulas 90, 92 for determining flow rate within the respective cannula(s). The curved portion 104 of the outer cannula 90 may be equipped with one or more fluid inlet apertures to facilitate the withdrawal of blood from right atrium 22 and/or right ventricle 30.

Figure 10:
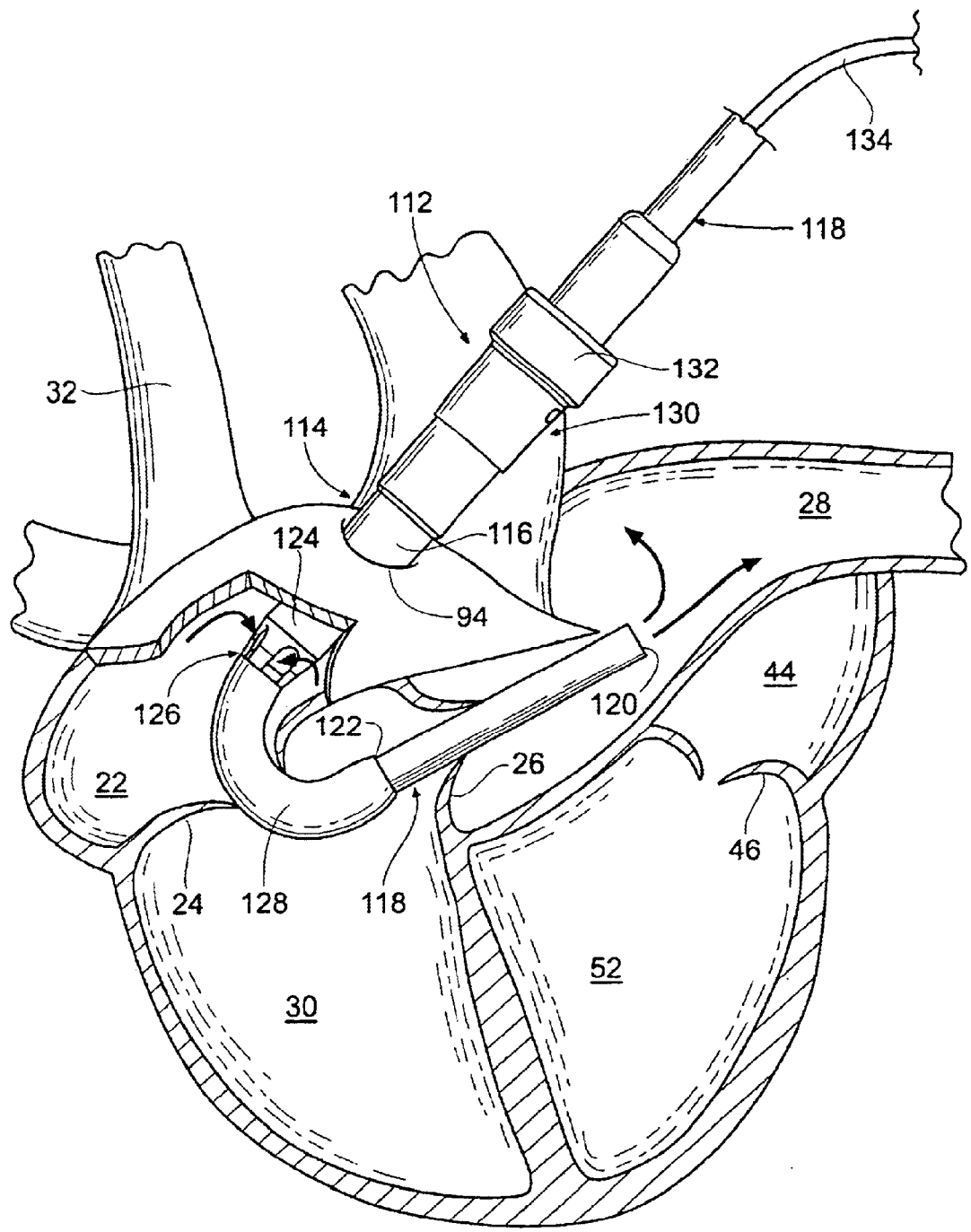
FIG. 10 is a sectional schematic view showing a dual cannula arrangement with an integrated pump assembly within a heart for providing right heart support during beating heart surgery according to the present invention.

FIG. 10 illustrates another dual lumen cannula and pump system for carrying out the methods of the present invention. In this embodiment, a pump and cannula system 112 comprises a dual cannula assembly 114 communicatively coupled to a pump (not shown) for supporting the right side of the heart during cardiac surgery. Pump and cannula system 112 is of the type shown and described in co-pending and commonly-assigned U.S. Provisional Patent App. Ser. No. 60/115,786, filed Jan. 13, 1999, the contents of which are incorporated by reference herein.

The pump and cannula system 112 is similar in many respects to the pump and cannula system 86 described above with reference to FIGS. 7–9, except that the pump (not shown) is integrated into the dual cannula assembly 114 such that it pumps blood from the right atrium 22 directly into the pulmonary artery 28 without being first transported outside the heart. The dual cannula assembly 114 includes an outer cannula 116 adapted to be introduced into the heart through the atrial appendage 94, and an inner cannula 118 disposed generally concentrically within the outer cannula 116 and having a distal end 120 adapted to extend, in use, past a distal end 122 of the outer cannula 116 and a sufficient length into the pulmonary artery 28. The outer cannula 116 includes a main body 124, an inflow port 126, and a curved portion 128. A miniaturized pump (not shown) is coupled to or forms part of the inner cannula 118 such that, when the inner cannula 118 is advanced within the outer cannula 116 as shown, the pump will be disposed within the curved portion 128 of the outer cannula 116. A Y-connector 130 coupled to the proximal end of the main body 124 contains a hemostasis valve 132 which can seal around the inner cannula 118. A sheathed power cable or drive shaft 134 may be extended through the inner cannula 118 depending upon whether the motor (not shown) for driving the pump is disposed within the dual cannula assembly 114 or located external to the dual cannula assembly 114. In some embodiments, the inner cannula 118 may be positioned entirely within the outer cannula 116, in which case the hemostasis valve 132 will seal around the sheathed power cable or drive shaft 143. In either event, the hemostasis valve 132 reduces the possibility of blood leakage or emboli forming within the patient's blood stream. The inner cannula 118 and outer cannula 116 combine to provide a protected blood flow path within the right side of the heart. Under the direction of the pump, blood from within the right atrium 22 may be selectively transported directly through the inner cannula 118 into the pulmonary artery 28. In this fashion, the pump and cannula system 112 may be utilized to provide right heart support to overcome any of the above-identified compromise conditions in cardiac output that may occur during beating heart surgery to avoid the need for CPB.

The methods of the present invention may also be accomplished through the use of any of a variety of pump and cannula systems having dual lumen cannula assemblies capable of entering the heart intravascularly, such as through the superior and/or inferior vena cava after entering the vasculature through the femoral and/or jugular vein. Exemplary embodiments of such intravascular dual cannula assemblies will be described below with reference to FIGS. 11–18, which intravascular cannula assemblies are shown and described in co-pending and commonly-assigned Int'l Patent App. Ser. No. PCT/US99/19537, filed Aug. 27, 1999, which claims priority to U.S. Provisional Patent App. Ser. No. 60/098,118, filed Aug. 27, 1998, the contents of which are incorporated by reference herein. In each instance, the dual lumen cannula assemblies, when placed within the heart, create a protected blood flow path such that the associated pump can maintain at least partial blood flow therethrough during beating heart surgery, regardless of any compromise condition in cardiac output that may occur, such as reduced cardiac output due to collapse or kinking of the vessels or heart chambers when the heart is lifted or manipulated during surgery. As will be appreciated, the various intravascular dual cannula assemblies described herein may be employed with any of the above-described pumping arrangements (including but not limited to reverse flow, axial flow, centrifugal flow, and roller types) to provide right and/or left heart support during cardiac surgery according to the present invention.

Figure 11:
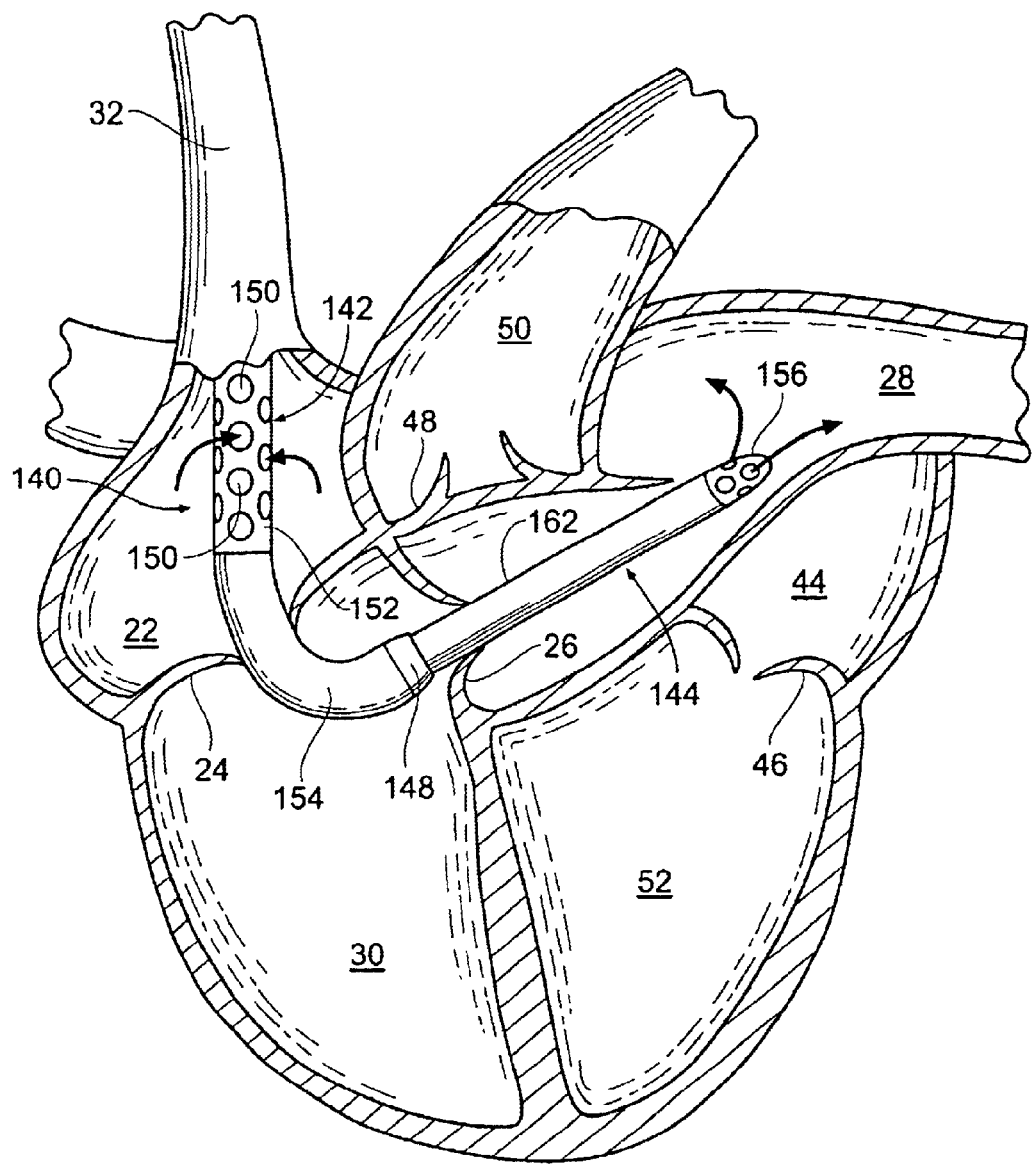
FIG. 11 is a sectional schematic view showing an intravascular dual cannula arrangement within a heart for providing right heart support during beating heart surgery according to the present invention.
Figures 12, 13:
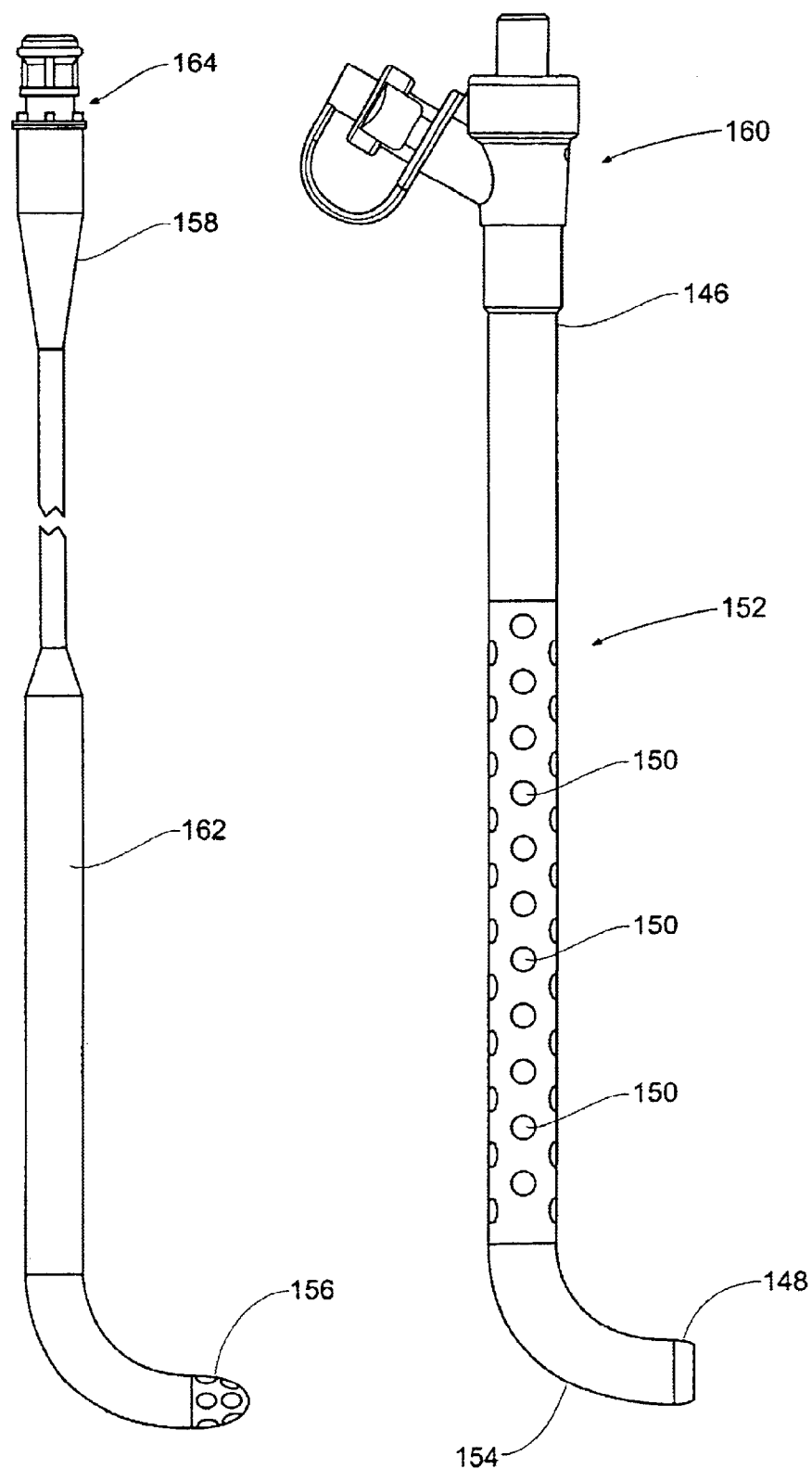
FIG. 12 is a side view of an inner cannula of the intravascular dual cannula arrangement shown in FIG. 11.
FIG. 13 is a side view of an outer cannula of the intravascular dual cannula arrangement shown in FIG. 11.

FIGS. 11–13 illustrate an exemplary embodiment of an intravascular cannula assembly 140 for carrying out a method of providing right heart support during cardiac surgery according to the present invention. The cannula assembly 140 of this embodiment includes an outer cannula 142 dimensioned to receive an inner cannula 144 through an interior lumen (not shown) extending between a proximal end 146 and a distal end 148. The outer cannula 142 includes a plurality of fluid inlet apertures 150 disposed along a main body portion 152, and a curved portion 154 extending distally from the main body portion 152. In use, the outer cannula 142 is introduced into the vasculature of the patient and advanced into the heart such that the plurality of fluid inlet apertures 150 are preferably disposed within the right atrium 22. The curved portion 154 is preferably dimensioned such that, in use, it extends through the tricuspid valve 24 and into the right ventricle 30 such that an aperture (not shown) in its distal end 148 is directed generally at the pulmonary valve 26. As will be appreciated, the curved portion 154 of the outer cannula 142 thus serves a guiding function that facilitates the placement of the inner cannula 144 into the pulmonary artery 28 according to the present invention. The inner cannula 144 is disposed generally concentrically within an outer cannula 142 and includes a distal end 156 that extends, in use, past the distal end 148 of the outer cannula 142, through the pulmonary valve 26, and a sufficient distance into the pulmonary artery 28. In use, the proximal ends 146, 158 of the outer and inner cannulas 142, 144 lie outside the patient's body and are communicatively coupled to any of a variety of pumping arrangements (not shown). The pump, which may comprise any of the variety disclosed herein, may be selectively operated (i.e. automatically or on-demand) to withdraw blood from the right atrium 22 through a flow path defined by the generally annular space between the interior surface of the outer cannula 142 and the interior surface of the inner cannula 144 and transport this blood through a flow path defined within the lumen of the inner cannula 144 for deposit into the pulmonary artery 28. In this fashion, the intravascular cannula assembly 140 establishes a protected blood flow path within portions of the right heart such that, under the direction of the pump (not shown), at least partial blood flow may be maintained during cardiac surgery so as to avoid the need for CPB.

As shown in FIG. 13, a Y-connector 160 is provided coupled to the outer cannula 142 such that the inner cannula 144 may be slideably advanced through the outer cannula 142 according to the present invention without resulting in blood leakage or the formation of air emboli within the patient's blood. It will be readily understood that Y-connector 160 is presented by way of example only and that the cannula assembly 140 of the present invention is not dependent upon a particular type of connector. As shown in FIG. 12, the inner cannula 144 comprises a substantially tubular structure having a wall 162 defining an internally disposed lumen (not shown). The inner cannula 144 is provided at its proximal end 158 with a connector 164, which is suitably sized to interface with the given pumping arrangement. The length of the outer and inner cannulas 142, 144 is application specific and depends for example on the size of the patient and the distance from the access point into the patient's vasculature (i.e. an incision in the neck) to the destination in the patient's pulmonary system. In a CABG application, for example, the pulmonary artery is a destination into which blood may be returned into the patient from the pump system via the inner cannula 144, and the dimensions of the inner cannula 144 are selected accordingly. The inner cannula 144 may be provided with one or more fluid outlet apertures 166 disposed at the distal end 156, or (although not shown) may be open-ended with a single fluid outlet aperture, in order to facilitate the deposit of blood into the pulmonary artery 28.

The outer and inner cannulas 142, 144 can be formed of materials ranging from rigid to flexible, and in the preferred embodiment comprise a semi-rigid transparent material such as polyurethane or silicone having a hardness of between about 30A and 90A on a Shore durometer scale and capable of withstanding sterilization by ethylene oxide (ETO). Rigid clear materials can be used for the y-connector 160, and preferably y-connector 160 is constructed of polycarbonate or polyvinyl chloride. The outer and inner cannulas 142, 144 may also contain radiopaque markings (not shown) to determine placement within the patient's body. To provide structural reinforcement, a spiraling wire (not shown) can be provided for support of the walls of the outer and inner cannulas 142, 144. The spiraling wire (not shown) may be molded into the walls or is otherwise supported therein, and may extend either partially or fully across the length of the cannulas 142, 144. The wire facilitates handling of the cannulas and reduces the possibility of the cannulas' collapsing or being pinched shut and thus closing off the flow of fluid to or from the patient. Other ways of reinforcing the tubular bodies of the cannulas 142, 144 are known in the art and will adapt equally well to the present invention. Such reinforcement may be omitted if the cannula material is sufficiently rigid or if sufficient fluid flow is present within the cannulas 142, 144.

One or more pre-formed curves may be provided in the outer and/or inner cannulas 142, 144. As will be appreciated, such preformed curves serve to facilitate cannula maneuverability during insertion in the patient's body, permitting the negotiation of tortuous passages such as through the atria, ventricular valve and pulmonary valve. The angle of the pre-formed curves may be anywhere in the range of 0–180 degrees, with the curves being disposed anywhere along the length of the cannulas 142, 144 and in any one or more distinct planes, depending on the particular application. The curves may also be of an adjustable angle, formed by expandable joints, such as through the use memory shaped material which, in the presence of current, will either change length or shape depending upon the characteristics of material used. An example of such a material is Nitinol, commercially available from Educational Innovations, Inc. 151 River Road, Cos Cab Conn. 06807. If imbedded within the walls of the cannulas 142, 144 and activated with electrical current, Nitonol may allow an operator to selectively alter the position and orientation of distal ends 148, 156. In another construction, auxiliary lumens may be provided within the walls of the outer and/or inner cannulas 142, 144 such that cables or wires may be selectively introduced therein and employed to impart or relieve forces so as to induce deformation and curvature of the outer and/or inner cannula 142, 144.

The cannula assembly 140 may be introduced into the patient's vasculature to achieve the intravascular access into the heart through any number of access points, including but not limited to the internal jugular vein, the brachiocephalic vein, carotid artery, axillary artery, and femoral vein. As is well known in the art, such intravascular access may be achieved through the use of the Seldinger technique. Generally speaking, this procedure involves locating and piercing the patient's target vessel using a long, hollow needle attached to a syringe. When blood enters the syringe, the distal end of a thin guide wire is inserted through the needle and into the target vessel. The needle is then removed, leaving guide wire in place in the target vessel. The proximal end of the guide wire is then passed through a dilator, which is disposed axially within the outer cannula 142 such that its end protrudes through the distal tip 148 thereof. (At this point, the outer cannula 142 does not contain the inner cannula 144—that is, the cannula assembly 140 is not in the assembled configuration). The distal end of the dilator is then inserted into the target vessel so as to expand the incision. The outer cannula 142 may then be advanced into position, either partially or fully, within the target vessel, after which point the dilator is then withdrawn. The inner cannula 144 can then be inserted through the outer cannula 142 form the cannula assembly 140, which insertion can be achieved in one of several ways. One option involves advancing a balloon catheter (not shown) through the outer cannula 142 such that the balloon is positioned in a desired location within the heart (i.e. the pulmonary artery) under the direction of the natural blood flow. The inner cannula 144 may then be threaded over the balloon catheter and advanced into position within the desired location, after which point the balloon catheter may be withdrawn. A second option for inserting inner cannula 144 into position within the patient's body is to use a guide wire to guide the inner cannula 144 to its final destination. A particularly suitable guide wire for this would be one of the J-hook type which would facilitate negotiation of the tortuous turns involved, especially between the right atrium 22 and pulmonary artery 28. As discussed above, this negotiation may be further facilitated by providing the inner cannula 144 with one or more preformed curves (i.e. on or near the distal end 156). It should also be recognized that a guidewire may be inserted into a balloon catheter to stiffen the balloon catheter and thereby facilitate its placement within the patient's body.

A major advantage of the foregoing intravascular cannulation arrangement is the placement of the pump system and attendant connections, sensors, and other equipment out of the immediate vicinity of the beating heart surgical procedure, thereby freeing up space in which the surgeon can operate. Other advantages include a low priming volume requirement as the pump system can be located closer to the patient's body (i.e. near the patient's neck region) since that region is not being operated on. Additionally, the insertion procedure for the cannulation assembly 140 can be performed prior to the surgical operation, by someone other than the surgeon, such as the anesthesiologist, thereby reducing the length of time required for the heart surgery itself. More importantly, however, the intravascular cannulation arrangement described above provides yet another manner of establishing a protected blood flow path within the heart (the right side, in the embodiment shown above), such that a pump can be selectively employed to maintain at least partial blood flow through the protected blood flow path during beating heart surgery. In this fashion, the intravascular cannulation arrangement provides the same advantages as the other cannula arrangements disclosed herein, namely, it advantageously overcomes any of the above-identified conditions when cardiac output may become compromised during beating heart surgery, thereby avoiding the need for CPB.

Figure 14:
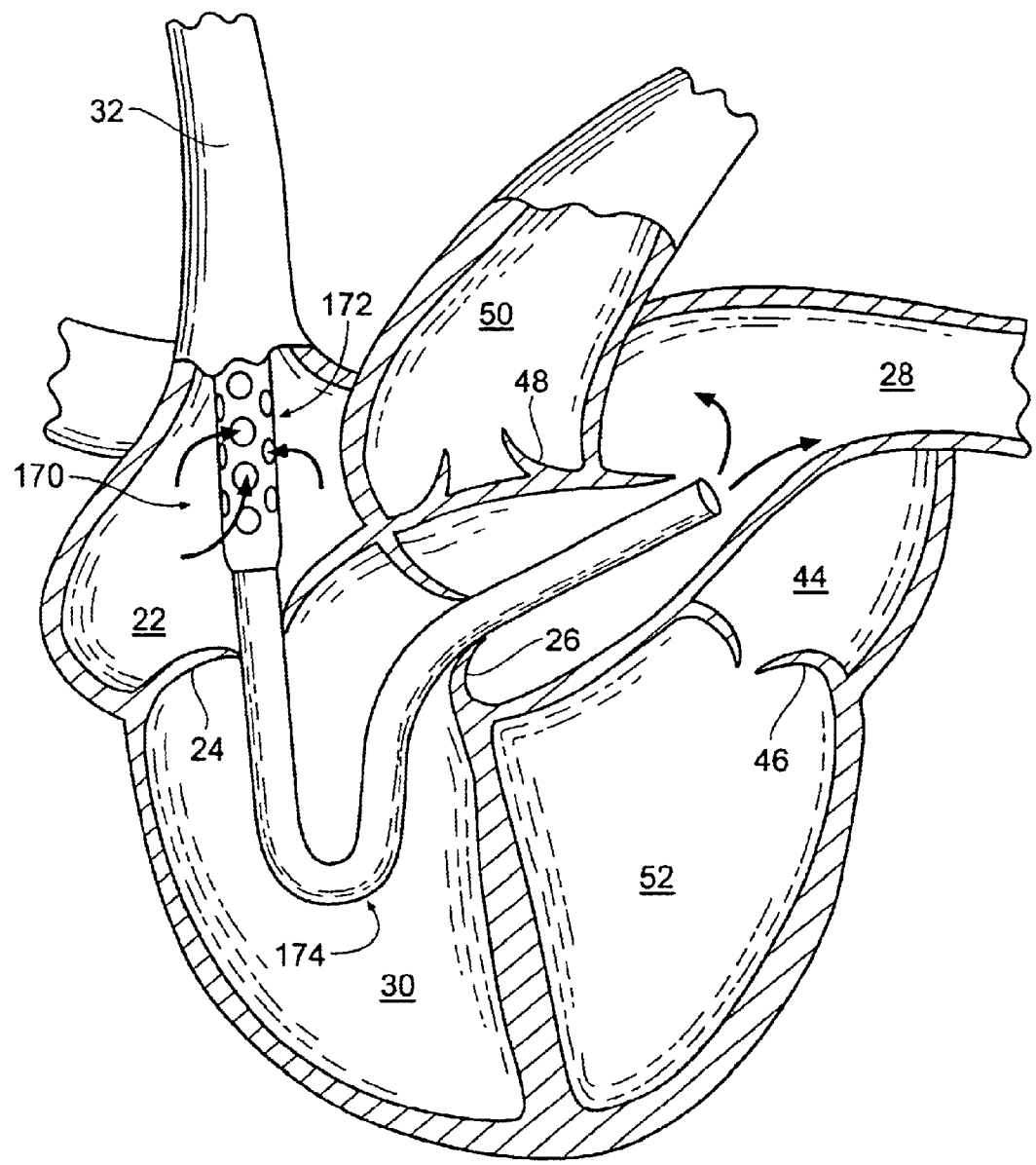
FIG. 14 is a sectional schematic view of another intravascular dual cannula arrangement within a heart for providing right heart support during beating heart surgery according to the present invention.

The foregoing intravascular cannula assembly 140 is set forth by way of example only, and it is to be readily understood that any number of additional intravascular cannula assemblies may be employed without departing from the scope of the present invention. For example, FIG. 14 illustrates an intravascular cannula assembly 170 for use in providing right heart support during beating heart surgery. The cannula assembly 170 is similar in virtually all respects to the intravascular cannula assembly 140 described above with reference to FIG. 11, except that the outer cannula 172 does not includes a curved portion such that the inner cannula 174 must be advanced through the tricuspid valve 24, the right ventricle 30, the pulmonary valve 26, and a sufficient distance into the pulmonary artery 28 without the guiding function of the curved portion 154 shown in FIGS. 11 and 13. The placement of the inner cannula 174 may be accomplished through the use of any known guiding mechanism in the prior art. These may include, but are not necessarily limited to, the use of an inflatable balloon catheter, providing an inflatable balloon on the distal end of the inner cannula 174 itself, or employing guidewires or other mechanisms for selectively altering the configuration of the inner cannula 174 to assist in negotiating the tortuous pathway to place the distal end 176 into the desired location in the heart. In all other respects, the intravascular cannula assembly 170 is identical in operation and construction as that shown and described with reference to FIGS. 11–13 such that a duplicate discussion is not necessary.

Figure 15:
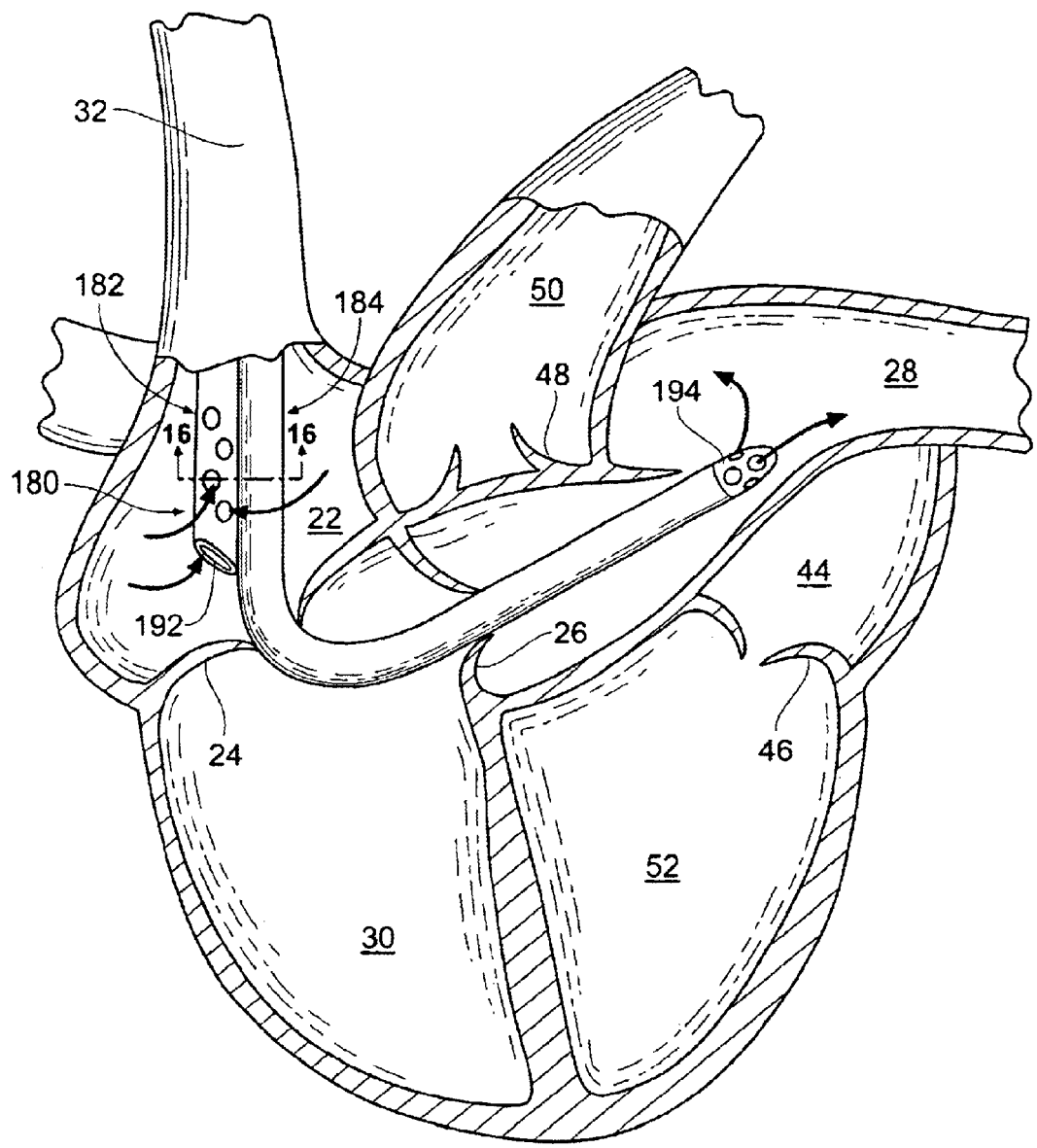
FIG. 15 is a sectional schematic view showing another intravascular dual cannula arrangement within a heart for providing right heart support during beating heart surgery according to the present invention.

The intravascular cannulation assemblies for use in carrying out the methods of the present invention may also take the form a pair of cannulas disposed in slideable and side-by-side relation. FIG. 15 illustrates one such intravascular cannula assembly 180 for use in providing right heart support during beating heart surgery. The cannula assembly 180 includes a first cannula 182 slideably coupled to a second cannula 184. As with the foregoing embodiments, the proximal ends (not shown) of the first and second cannulas 182, 184 are communicatively coupled to a pump (not shown) that may be selectively operated to withdraw and reintroduce blood between various points in the heart. FIGS. 16A–16D illustrate a variety of exemplary coupling mechanisms 186 that can be employed to provide the slideable relation between the first cannula 182 and second cannula 184. In the embodiments shown, coupling mechanisms 186 generally comprise an elongated engagement member 188 disposed along all or certain portions of one of the two cannulas 182, 184 capable of matingly engaging with an elongated groove or channel 190 disposed along all or certain portions of the other cannula 182, 184. In an important aspect, this allows the user great flexibility in selectively positioning the distal tip 192 of the first cannula 182 and the distal tip 194 of the second cannula 184 at predetermined positions within the heart. For example, with reference to FIG. 15, the slideable function of the coupling mechanism 186 may be employed to selectively position the distal end 192 of cannula 182 in a first predetermined location (i.e. in the right atrium 22) and selectively position the distal end 194 of cannula 184 in a second predetermined location (i.e. in the pulmonary artery 28). In this fashion, the first conduit 182 may be used as an inflow conduit to the externally located pump for the purpose of withdrawing blood from the right atrium 22, and the second conduit 184 may be used as an outflow conduit from the pump for the purpose of depositing this blood into the pulmonary artery 28.

As with the previously described intravascular cannula assemblies, the cannula assembly 180 of this embodiment may be introduced into the patient's vasculature by utilizing the Seldinger technique as described above. It will be appreciated that the engagement members which form part of the coupling mechanism 186 may extend along all or portions of the respective length of the cannula 182, 184. Also, as illustrated in FIGS. 17 and 18A–18B, the slideable coupling mechanism between the individual cannulas 182, 184 may also be constructed from one or more barrel portions 196 fixedly attached to the first cannula 182. In so doing, the first and second cannulas 182, 184 may be selectively positioned independent of the other based on this slideable coupling. It should also be understood that, although the foregoing intravascular cannula arrangements have been shown and described for use in providing right heart support, this does not limit the applications of this invention for use in right heart support only. Rather, the intravascular cannula arrangements shown herein are equally applicable in providing left heart support during beating heart surgery according to the methods of the present invention.

Figure 19:
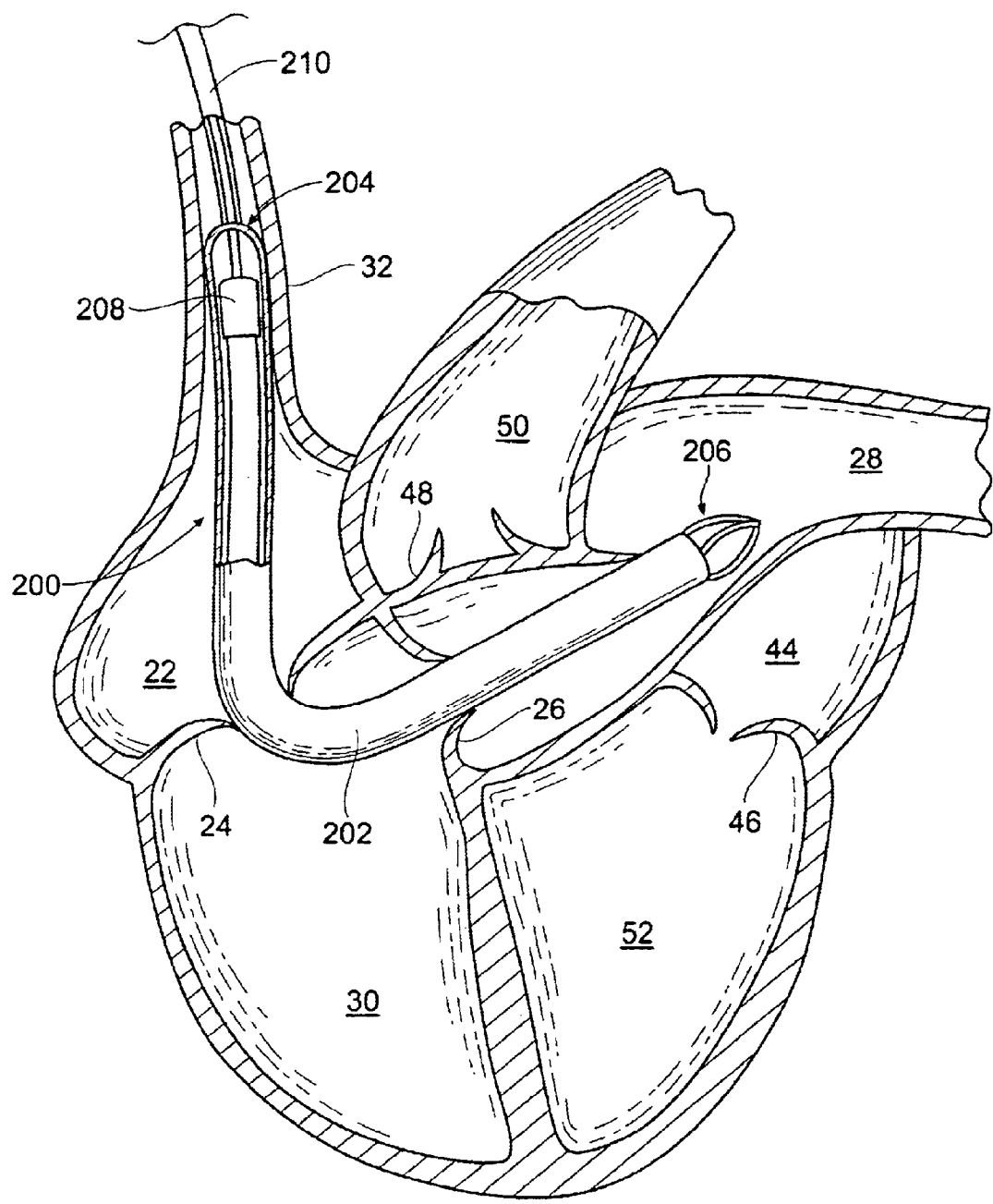
FIG. 19 is a sectional schematic view illustrating an intravascular pump and cannula system within a heart for providing right heart support during beating heart surgery according to the present invention.
Figure 20:
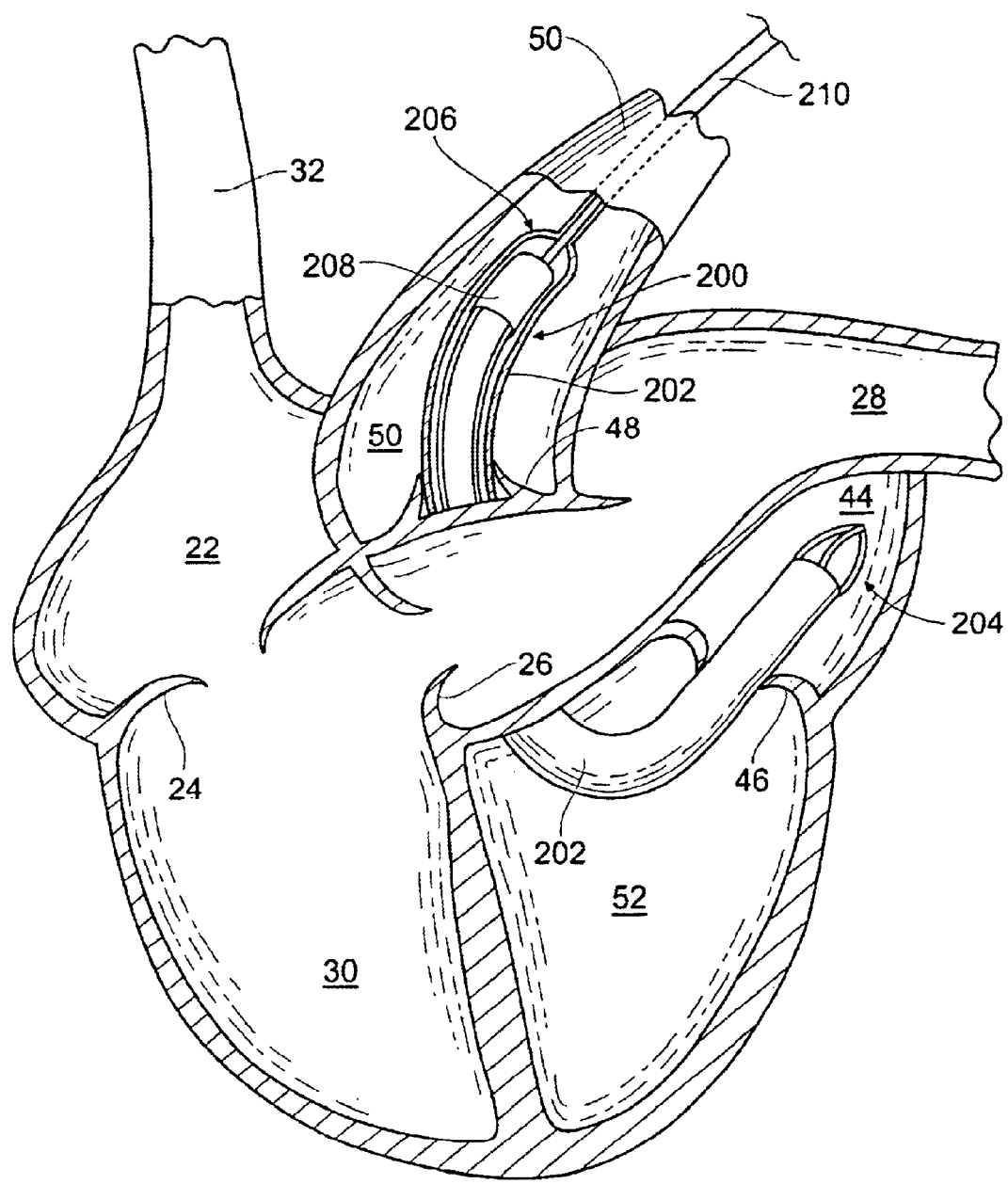
FIG. 20 is a sectional schematic view illustrating an intravascular pump and cannula system within a heart for providing left heart support during beating heart surgery according to the present invention.

FIGS. 19–20 illustrate a still further pump and cannula system 200 for carrying out the methods of performing beating heart surgery according to the present invention. In FIG. 19, the intravascular pump and cannula system 200 is shown positioned within the heart to provide right heart support during beating heart surgery. In FIG. 20, the intravascular pump and cannula system 200 is shown positioned within the heart to provide left heart support during beating heart surgery. Intravascular pump and cannula system 200 is of the type shown and described in co-pending and commonly-assigned U.S. Provisional Patent App. Ser. No. 60/152,249, filed Sep. 3, 1999, the contents of which is incorporated by reference herein.

The intravascular pump and cannula assembly 200 includes a single cannula 202 having a fluid inlet 204 at one end and a fluid outlet 206 at an opposite end, and an internally disposed pump 208 for transporting blood from the fluid inlet 204 to the fluid outlet 206. A cable assembly 210 is preferably provided coupled to the pump 208 for selectively controlling the operation of the pump 208 depending upon the particular pumping needs. For right heart support, the intravascular pump and cannula assembly 200 may be introduced into the patient's vasculature (in the manner described above) and advanced into the position shown in FIG. 19 such that the fluid inlet 204 is disposed within the vena cava (or right atrium) and the fluid outlet 206 is positioned within the pulmonary artery 28. The pump 208 may then be selectively (i.e. automatically or on-demand) controlled to transport blood from the vena cava (or right atrium) through the tricuspid valve 24, the right ventricle 30, and the pulmonary valve 26 for deposit within the pulmonary artery 28. For left heart support, the intravascular pump and cannula assembly 200 may be introduced into the patient's vasculature (in the manner described above) and advanced into the position shown in FIG. 20 such that the fluid inlet 204 is disposed within the left atrium 44 and the fluid outlet 206 is positioned within the aorta 50. The pump 208 may then be selectively controlled to transport blood from the left atrium 44 through the bicuspid valve 46, the left ventricle 52, and the aortic valve 48 for deposit into the aorta 50. The cannula 202 may thus be employed to establish a protected blood flow path within the right and/or left sides of the heart, and the pump 208 employed to maintain at least partial blood flow therethrough to overcome any compromise conditions in cardiac output, thereby avoiding the need for CPB during beating heart surgery.

Various pump and cannula arrangements have been described and shown above for providing right and/or left heart support wherein blood is deliberately re-routed through and past the right and/or left ventricle in an effort to reduce the volume of blood to be pumped by the particular ventricle. While "unloading" the ventricles in this fashion is preferred in certain instances, it is to be readily understood that the pump and cannula arrangements described herein may also be employed to "preload" the ventricles. Ventricular preloading may be accomplished by positioning the outflow cannula from the pump into a given ventricle such that the pump may be employed to fill or preload the ventricle with blood. This may be particularly useful with the right ventricle. On occasion, the right ventricle is not supplied with sufficient levels of blood from the right atrium such that, upon contraction, the right ventricle delivers an insufficient quantity of blood to the pulmonary artery. This may result when the right ventricle and/or right atrium are in a stressed or distorted condition during surgery. Preloading overcomes this problem by actively supplying blood into the right ventricle, thereby facilitating the delivery of blood into the pulmonary artery. The same technique can be used to preload the left ventricle and thus facilitate the delivery of blood from the left ventricle into the aorta.

Figure 21:
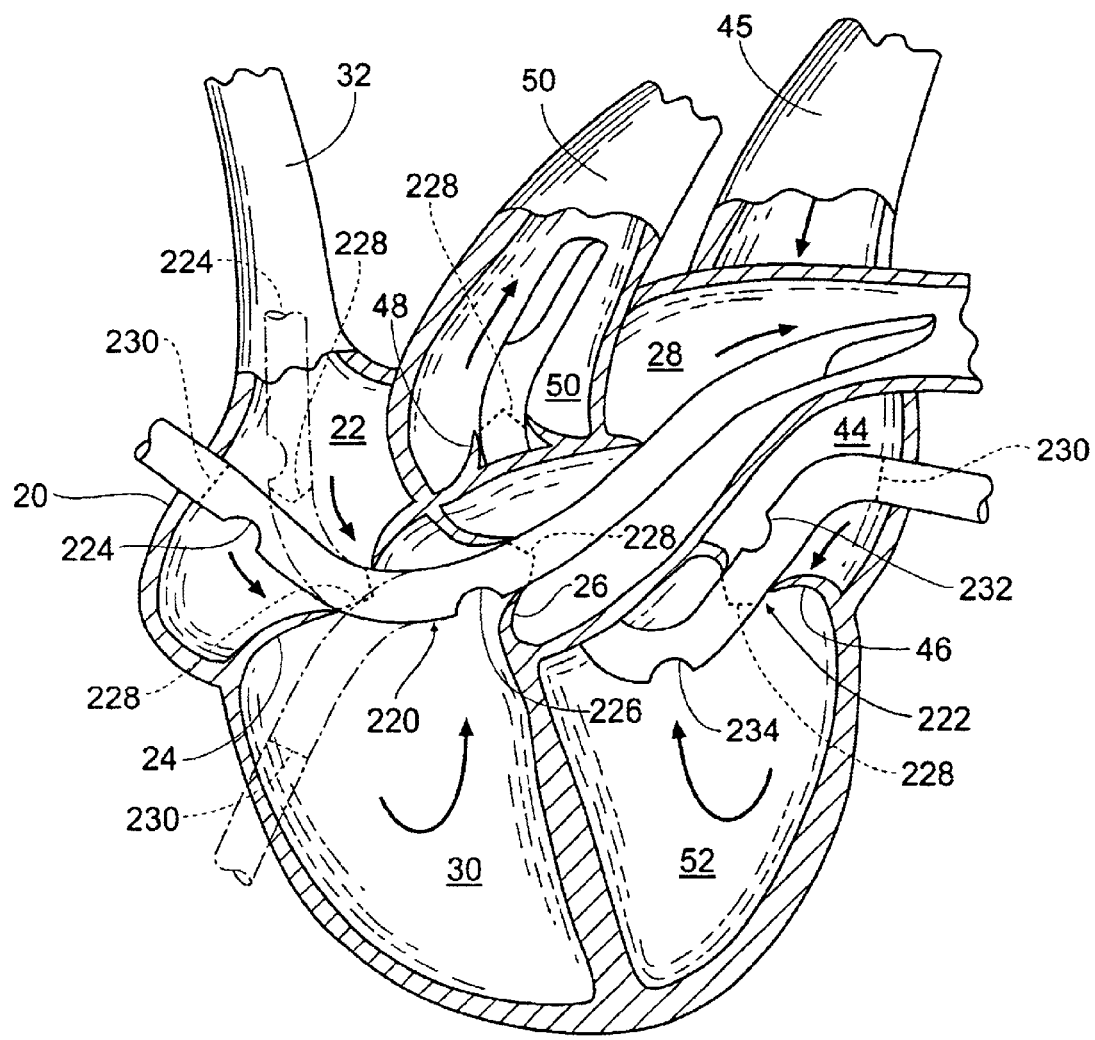
FIG. 21 is a sectional schematic view illustrating first and second valved cannulas within a heart for providing right and/or left heart support during beating heart surgery according to the present invention.
Figure 22:
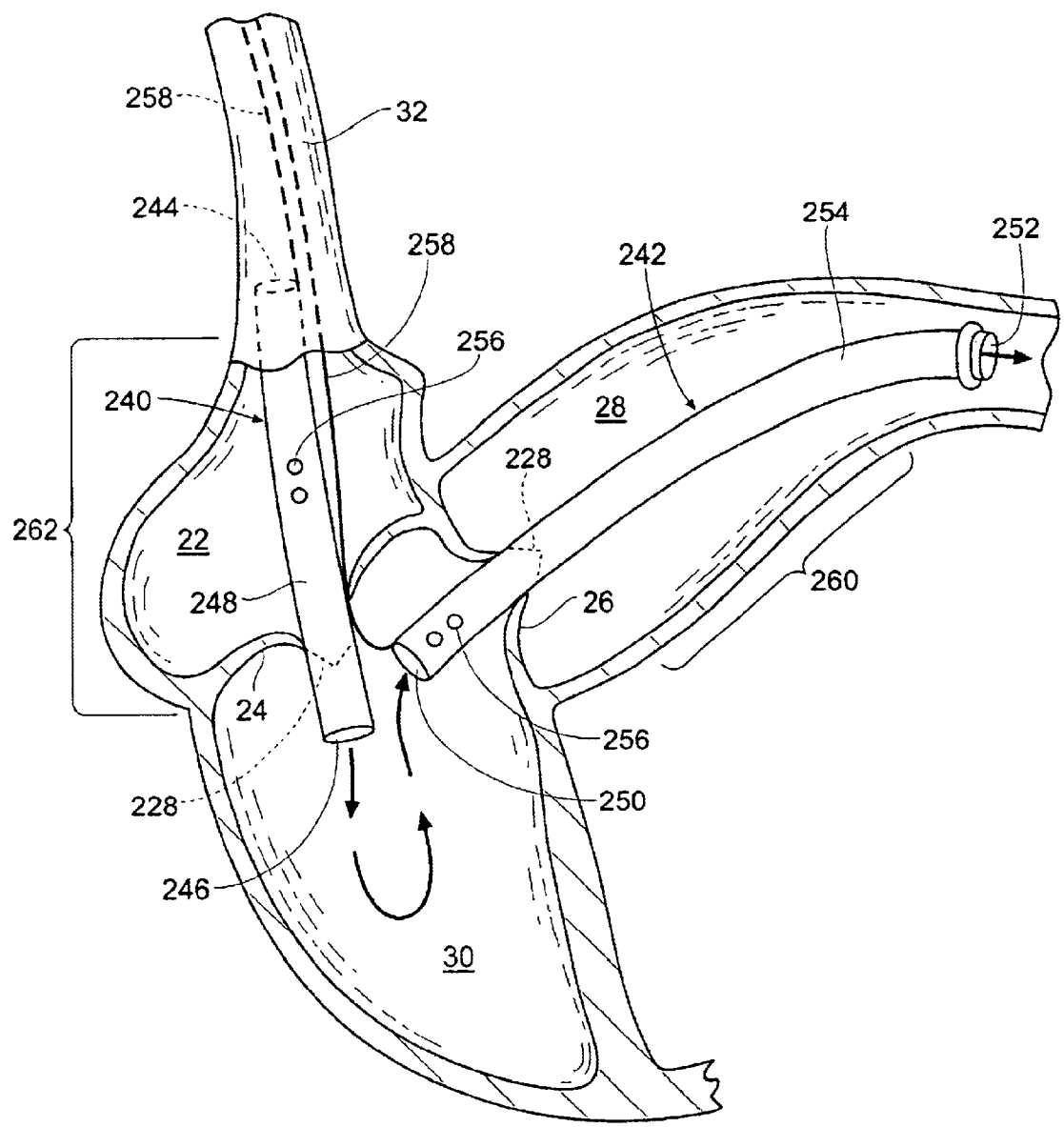
FIG. 22 is a sectional schematic view illustrating first and second valved cannulas within a heart for providing right heart support during beating heart surgery according to the present invention.
Figure 23:
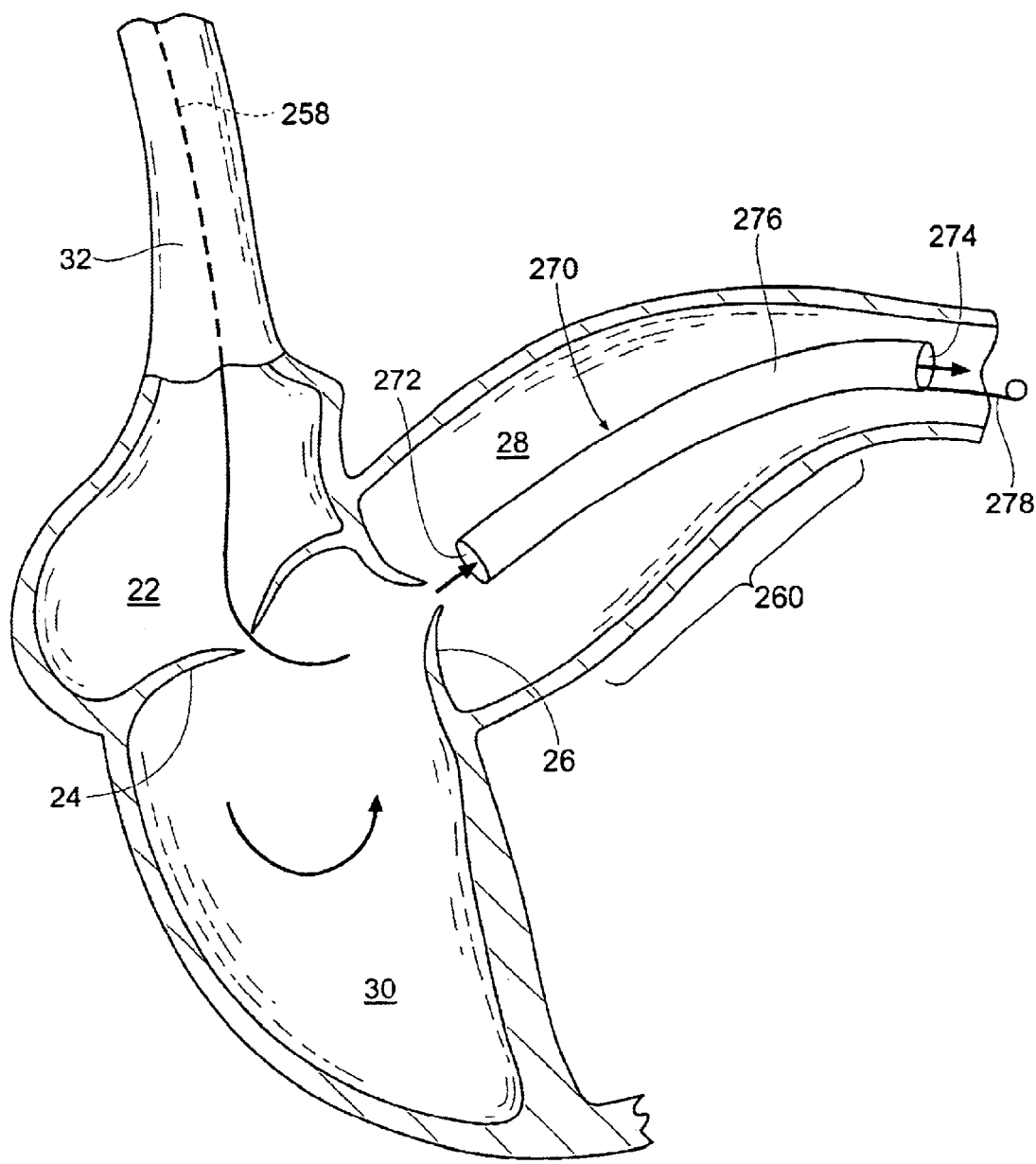
FIG. 23 is a sectional schematic view illustrating a stent within a heart for providing right heart support during beating heart surgery according to the present invention.

FIGS. 21–23 set forth exemplary embodiments of the second main system for carrying out the methods of performing beating heart surgery according to the present invention. The common denominator between all embodiments is the use of at least one conduit (cannula and/or stent) positioned within at least a portion of the right and/or left heart to establish a protected blood flow path such that the action of the beating heart can maintain at least partial blood flow therethrough during beating heart surgery. The cannula and/or stent embodiments are of the type shown and described in described in co-pending and commonly-assigned U.S. patent application Ser. No. 09/231,320, filed Jan. 13, 1999, which claims priority to U.S. patent application Ser. No. 09/079,836, filed May 15, 1998, the contents of which are hereby incorporated herein by reference. In this system, no pump is provided and the blood flow is provided solely by the beating heart. As such, this system is adapted for use exclusively in beating heart procedures. By protecting the blood path from restriction or collapse, the cannulas and/or stents assure the output of the beating heart is available at all times during the surgery to sustain the patient during surgery with sufficient pulmonary and circulatory blood flow. The protected blood flow path established within the right and/or left side(s) of the heart thereby serves to overcome compromise conditions in cardiac output, such as reduced or diminished blood flow due to kinking or collapse in the atria, ventricles, vena cava, pulmonary artery, and/or aorta that may occur when the heart must be lifted or manipulated to gain surgical access to anterior lateral and posterior blood vessels. In so doing, the cannulas and/or stents of the present invention obviate the need for CPB during beating heart surgery.

FIG. 21 illustrates first and second cannula arrangements for carrying out the methods of performing beating heart surgery according to the present invention. A first cannula 220 is provided for establishing a protected blood flow path within portions of the right side of the heart to provide right heart support during beating heart surgery. An optional second cannula 222 is provided for establishing a protected blood flow path within the left side of the heart to provide left heart support during beating heart surgery. In the main embodiment shown, the first cannula 220 is a generally tubular hollow structure which is introduced into the heart through an incision in the wall 20 of the right atrium 22, after which point it passes through the tricuspid valve 24, the right ventricle 30, the pulmonary valve 26, and a sufficient distance into the pulmonary artery 28. The cannula 220 is preferably equipped with a fluid inlet aperture 224 in the right atrium 22 and a fluid inlet aperture 226 in the right ventricle 30 which, under the pumping action of the heart, permit blood to enter the protected flow path within the cannula 220 for passage into the right ventricle 30 and onward into the pulmonary artery 28. Internal valves 228 are preferably provided within the cannula 220 (at or near the tricuspid valve 24 and pulmonary valve 26) so as to prevent unwanted back flow of blood from the right ventricle 30 into the right atrium 22 and from the pulmonary artery 28 into the right ventricle 30. The internal valves 228 may comprise any suitable mechanism for preventing back flow, including but not limited to a oneway or check valve such as a flap valve, a slide valve, a spring loaded circular valve or ball valve, a membrane valve, a duck bill valve, or any other valve design capable of functioning to prevent blood back flow. As shown in phantom, the cannula 220 may also be introduced into the heart in alternate fashions. For example, the cannula 220 may be introduced through an incision in the wall of the right ventricle 30 before passing through the right ventricle 30, the pulmonary artery 26, and into the pulmonary artery 28. In both of these embodiments, the cannula 220 should preferably be equipped with fluid plugs 230 at or near the junction where it passes through the wall of the heart to prevent the leakage of blood out the incision. The cannula 220 may also be introduced into the heart intravascularly from an incision in another part of the body such as a femoral vein or jugular vein or other desired access point. For example, as shown in phantom, the cannula 220 may be introduced intravascularly such that it enters the right atrium 22 through the superior vena cava 32. Although not shown, it will be readily appreciated that the cannula 220 may similarly enter the right atrium 22 through the inferior vena cava.

The optional second cannula 222 is a generally tubular hollow structure which is introduced into the heart through an incision in the wall of the left atrium 44, after which point it passes through the bicuspid valve 46, the left ventricle 52, the aortic valve 48, and a sufficient distance into the aorta 50. The cannula 222 is preferably equipped with a fluid inlet aperture 232 in the left atrium 44 and a fluid inlet aperture 234 in the left ventricle 52 which, under the pumping action of the heart, permit blood to enter the protected flow path within the cannula 222 for passage into the left ventricle 52 and onward into the aorta 50 to maintain at least partial circulatory blood flow during beating heart surgery. As with the pulmonary valve 220 described above, internal valves 228 are preferably provided within the cannula 222 (at or near the bicuspid valve 46 and aortic valve 48) so as to prevent unwanted back flow of blood from the left ventricle 52 into the left atrium 44 and from the aorta 50 into the left ventricle 52. The internal valves 228 may similarly comprise any suitable mechanism for preventing back flow, such as those enumerated by way of example with regard to the pulmonary cannula 220. Although not shown, the cannula 222 may also be introduced into the heart in number of alternate fashions, such as through an incision in the wall of the left ventricle 52, or intravascularly through the pulmonary vein 45. If passing through the wall of the heart, the cannula 222 should preferably be equipped with a fluid plug 230 at or near the incision to prevent the leakage of blood out the incision.

FIG. 22 illustrates additional cannula arrangements for carrying out the method of providing right heart support during beating heart surgery according to the present invention. A first cannula 240 is provided having a fluid inlet 244 disposed in the vena cava 32, a fluid outlet 246 disposed in the right ventricle 30, and a generally tubular hollow body 248 extending therebetween for establishing a protected blood flow path within portions of the vena cava 32, right atrium 22, and right ventricle 30. A second cannula 242 is provided having a fluid inlet 250 disposed within the right ventricle 30, a fluid outlet 252 disposed within the pulmonary artery 28, and a generally tubular hollow body 254 for establishing a protected blood flow path within portions of the right ventricle 30 and pulmonary artery 28. Under the pumping action of the heart, the first cannula 240 permits blood to flow from the vena cava 32 and/or the right atrium 22 (through the protected flow path established within the first cannula 240) for passage into the right ventricle 30, while the second cannula 242 permits blood to flow from the right ventricle 30 (through the protected blood flow path established within the second cannula 242) for passage into the pulmonary artery 28. Optional fluid inlet apertures 256 may be provided to facilitate the introduction of blood into the protected flow paths established within the cannulas 240, 242. Internal valves 228 are preferably provided within the cannulas (at or near the tricuspid valve 24 and pulmonary valve 26) so as to prevent unwanted back flow of blood from the right ventricle 30 into the right atrium 22 and from the pulmonary artery 28 into the right ventricle 30. The internal valves 228 may comprise any suitable mechanism for preventing back flow, including but not limited to those set forth by way of example in reference to FIG. 21. It should be noted that, like the pump and cannula systems discussed above, the cannulas described herein which are equipped with internal valves 228 may be employed to "preload" the ventricles. Such ventricular preloading may be accomplished by positioning the fluid outlet into a given ventricle such that the cannula may be employed to fill or preload the ventricle with blood. Handles 258 may also be provided for inserting the cannulas 240, 242 into proper position and for maintaining the them in the proper position during the beating heart bypass surgery procedure.

The first and second cannulas 240, 242 serve to prevent collapse and kinking within the right side of the heart such that, according to the present invention, at least partial pulmonary blood flow may be maintained by the action of the beating heart, thereby avoiding the need for CPB during beating heart surgery. More specifically, the establishment of a protected blood flow path ensures that blood may be routed through the right side of the heart under the pumping action of the heart, notwithstanding a compromise in cardiac output such as by a restriction in blood flow due to collapse or kinking that may occur in portions of the vena cava 32, right atrium 22, right ventricle 30 and/or pulmonary artery 28 when the beating heart is lifted and manipulated during beating heart bypass surgery in order for the surgeon to gain surgical and visual access to the lateral and posterior vessels of the heart. The length and actual area of the portions of the right heart which tend to collapse or kink may vary from patient to patient and vary depending on the bypass procedure being performed and the extent to which the heart is moved and manipulated. The area within the pulmonary artery 28 that is subject to such collapse or kinking (referred to generally as a "kink zone" and denoted for clarity at 260) may be the area extending about 15 cm from the pulmonary valve 26. In the embodiment shown, the pulmonary cannula 242 is positioned such that the fluid outlet 252 is disposed downstream of this kink zone 260. Another area (referred to generally as a "collapse zone" and denoted for clarity at 262) includes portions of the right atrium 22 and vena cava 32 that are subject to collapse or kinking when the heart is lifted or manipulated during beating heart surgery. In the embodiment shown, the atrial or tricuspid cannula 240 is positioned such that the fluid inlet 244 is disposed upstream of this collapse zone 262.

Cannulas 240, 242 can be introduced into the heart in any number of fashions. For example, as shown, cannulas 240, 242 may be inserted with handles 258 through the vena cava 32 after passing through an incision in the wall of the vena cava 32 or an incision in a remote vein, such as the femoral vein or jugular vein. Although not shown, the cannulas 240, 242 may also be inserted through an incision in the wall of the right atrium 22 or through an incision in the wall of the right ventricle 30. However, remote access incision is preferred in order to keep the heart relatively free of encumbrances and other incisions to enhance the access for beating heart bypass surgery. It should also be understood that, with cannulas 240, 242 in position, the beating heart blood flow may also be maintained around the outside of the cannulas. That is to say, the cannulas 240, 242 may be dimensioned such that blood may flow around the outside of the cannulas when the tricuspid valve 24 and pulmonary valve 26 open, and blood may flow through the interior of the cannulas when there is any constriction which prevents the blood flow around the outside of the particular cannula. In a preferred embodiment, the pulmonary cannula 242 may include a balloon tip at or near the fluid outlet 252 in order to aid in the insertion and proper positioning of the cannula 242 within the pulmonary artery 28. With the pulmonary cannula 242 is in position, the heart may be lifted and manipulated and, by virtue of the protected blood flow path established within or around the pulmonary cannula 242, at least partial blood flow through the kink zone 260 may be maintained by the pumping action of the heart. With the atrial or tricuspid cannula 240 in position, the heart may be lifted and manipulated and, by virtue of the protected blood flow path established within or around the cannula 240, at least partial blood flow through the collapse zone 262 may be maintained by the pumping action of the heart.

The configuration of the cannulas 240, 242 are presented in FIG. 22 by way of example only, and it is to be readily appreciated that these cannulas may be provided in any number of different fashions without departing from the scope of the present invention. For example, the portion of the cannulas 240, 242 which extends through and contacts the tricuspid valve 24 and pulmonary valve 26 may have a different outside diameter than the respective portions disposed in the right atrium 22, right ventricle 30, and pulmonary artery 28. It may be desirable in some patients to have the outside diameter of the cannulas 240, 242 at the valve contact portion smaller to allow the maximum beating heart blood flow around the outside of the cannulas when the respective valve opens. In other patients, it may be desirable to have a larger diameter at the portion at valve contact to maximize the beating heart blood flow through the cannula 240, 242 as opposed to around the cannula. The fluid inlets and outlets of the cannulas disclosed herein may also comprise conventional blood cannula configuration and/or can comprise orifices, slits or other openings at desired locations and intervals along portions of the length of the cannula basket or cage to prevent heart tissue suction. The ends or openings can comprise baskets, cages or other guards to prevent suction of heart tissue or blood vessel wall into the cannula.

It is also within the scope of the invention to connect the cannulas 240, 242 together to be operated as a single cannula, or to manufacture them as a single continuous cannula having the appropriate openings and internal valves 228 as described above. In this embodiment, such a single valved cannula can simultaneously establish a protected flow path extending through both the collapse zone 262 and the kink zone 260. An advantage of such a configuration would be that the cannula can be inserted through a single incision with a single guidewire or balloon for guidance, and employ a single handle 258 for positioning and holding the cannula in proper position during surgery. In another embodiment, the cannulas 240, 242 may be dimensioned so that one will nest or telescope inside the other during insertion, such as by providing one of the cannulas 240, 242 having a slightly smaller diameter so that it will nest inside the other cannula during insertion. In this fashion, the two cannulas 240, 242 can be inserted through a single incision and a single guidewire and/or balloon may be employed (preferably at the outlet end of one of the cannulas) to guide both cannulas into proper position. However, each cannula 240, 242 would preferably have a separate handle 258 for positioning and holding the respective cannula in position during surgery. In such an embodiment, the nested cannulas 240, 242 would be inserted through the appropriate incision and, when the atrial or tricuspid cannula 240 reaches its proper position at the collapse zone 262, the handle 258 may be used to hold cannula 240 in its proper position, while the pulmonary cannula 242 can continue on its path of insertion until it is properly positioned across the pulmonary valve 26 and into the kink zone 260 within the pulmonary artery 28. To facilitate this insertion and deployment process, the inner cannula (i.e. the atrial or tricuspid cannula 240) may be provided with an auxiliary lumen to pass the handle 258 of the outer cannula (i.e. the pulmonary cannula 242) therethrough. Other configurations and embodiments of the cannula system illustrated in FIG. 22 will be apparent to one skilled in the art. For example, although only the right side of the heart is shown, it will be equally apparent to one skilled in the art that the same cannula systems shown and described in FIG. 22 may be readily adapted for use in the left side of the heart for protection of the left atrium 44, left ventricle 52, and aorta 50 from collapse or kinking during beating heart bypass surgery.

FIG. 23 illustrates an exemplary stent arrangement for carrying out the methods of performing beating heart surgery according to the present invention. A stent member 270 is provided having a fluid inlet 272, a fluid outlet 274, and a generally tubular hollow body 276 extending therebetween to establish a protected blood flow path within the pulmonary artery 28. In the embodiment shown, the fluid inlet 272 is disposed near the pulmonary valve 26 and the fluid outlet 274 is disposed downstream from the kink zone 260. The stent 270 is preferably of sufficient size, strength and flexibility to provide protection against the pulmonary artery 28 becoming folded, kinked or otherwise obstructed when the heart is lifted and manipulated during beating heart bypass surgery for surgical access to the lateral or posterior vessels of the heart. Stent 270 may be sized to approximate the size of the pulmonary artery 28 in which it is placed so that essentially all of the beating heart blood flow passes through the interior of the stent 270 with a minimum amount, if any, of blood flow around the outside of the stent 270. An optional handle 258 may be employed for inserting the stent 270 through an appropriate incision, for holding the stent 270 in proper position during the beating heart bypass surgery, and for withdrawing the stent 270. The stent 270 may also be equipped with an optional guidewire/balloon portion 278 for facilitating the guidance of stent 270 through vena cava 32 and the heart chambers and valves as well as other blood vessels in order to properly position stent 270 and across the kink zone 260 of pulmonary artery 28.

In some patients undergoing beating bypass surgery, inserting the stent 270 protect the pulmonary artery 28 from blood flow compromise may be all that is required to assure that the beating heart blood flow is maintained during the beating heart bypass surgery. However, in other patients, and depending on the surgical procedure to be performed, other devices disclosed herein may be used in combination with stent 270. For example, it may be desirable to protect the right atrium 22 from collapse by also using atrial or tricuspid cannula 240 illustrated in FIG. 22, which cannula 240 can be inserted separately after stent 270 is inserted and properly placed. The cannula 240 may also be nested or telescoped with stent 270 (in the manner discussed above with reference to the cannulas 240, 242 of FIG. 22) so that they are inserted at the same time through the same incision, then separated at the time that they reach tricuspid valve 24 such that the cannula 240 is retained in proper position across the collapse zone 262 and the stent 270 is allowed to continue through right ventricle 30, the pulmonary valve 26, and positioned within the pulmonary artery 28. In another embodiment of this invention, a second stent can be used in addition to the pulmonary stent 270, wherein the second stent is positioned across collapse zone 262 of vena cava 32 and right atrium 22, preferably such that the fluid outlet of the second stent is positioned close to (but not extending through) the tricuspid valve 24. Such embodiment employing two stents, one positioned in collapse zone 262 and one positioned in kink zone 260, may provide sufficient protection in some patients for the beating heart blood flow during lifting and manipulation of the heart during beating heart bypass surgery. It is also within the scope of the invention to position members having no internal flow path within portions of the right and/or left heart for maintaining at least partial blood flow through the right and/or left sides during beating heart surgery. Such members may be a solid, flexible rod or a closed tube which provides support for preventing the collapse of the right and/or left sides of the heart. For example, one or more of such members having no internal flow may be positioned within the vena cava 32, the right atrium 22, right ventricle 30, and pulmonary artery 28 to provide a support structure around which the beating heart can continue to pump blood even though a portion of the right side of the heart may have folded or collapsed against a portion of the surface of the member, such as when the heart is lifted or manipulated during beating heart surgery.

As will be apparent, other combinations of the various embodiments of the present invention can be used as appropriate for a particular patient. For example, stent 270 may be positioned in kink zone 260 and used in combination with a right heart pump and cannula system as shown and described above with reference to FIGS. 1–20, except that the cannula of the pump and cannula system would preferably be modified to extend only into the right ventricle 30 and not through pulmonary valve 26. In such a combination, the pulmonary blood flow from vena cava 32 and right atrium 22 would not only be protected, but could be augmented and supplemented by a pump employed to transfer blood from the right atrium 22 into the right ventricle 30. As also will be apparent to one skilled in the art utilizing the disclosure of the present invention, the stent 270 can also be utilized for insertion into the left side of the heart to prevent the collapse, kinking or other restriction within areas subject to experience such conditions, such as may result within the aorta 50, right ventricle 52, left atrium 44, and pulmonary vein 45 when the heart is lifted or manipulated to gain surgical and visual access to the lateral and posterior vessels on the heart.

As will be recognized by one skilled in the art, the above discussed cannulas, stents, tubing and the like will obviously be made of appropriate flexible bio-compatible materials which have sufficient flexibility, radial stiffness and other strength properties appropriate to the function intended in this invention. In most applications the cannulas and stents utilized in this invention must have appropriate radial strength and stiffness to resist collapsing or kinking under the stresses and compressive loads imposed on them when inserted in the appropriate blood vessels and the heart lifted and manipulated during beating heart bypass surgery. In some instances, soft and flexible materials such as silicones may be desirable and may need to be reinforced with wire or other material to provide the radial stiffness and resistance to collapsing necessary to be useful in the present invention.

In another aspect, this invention provides apparatus and methods for placement and positioning of the stents and cannulas of this invention. In this aspect, a pressure transducer is provided on the end of the cannula or stent for detection of the blood pressure patterns present at the end of the cannula or stent. Since the pressure patterns are different and distinct in different parts of the system, the pressure transducer may be used to determine whether the end of the cannula or stent is in the vein, atrium, ventricle or artery. The pressure transducer on the end of the cannula or stent enables precise placement at the desired location. Multiple transducers may be used along the length of the cannula or stent or at both ends thereof to provide the information needed for precise placement of the cannula or stent. For example, side ports along the cannula with separate lumens for the transducer connecting wire can be used to provide desired information for monitoring the condition of the patient, such information is also useful in controlling the pumps in the pump and cannula system employed according to this invention.

There has been shown and described herein various systems for carrying of methods of beating heart cardiac surgery according to the present invention. In utilizing the various aspects and combinations of the present invention, the basic method of the present invention includes the first step of inserting into the patient the selected stents, cannulas and/or pump and cannula systems as appropriate for a particular patient and a particular surgical procedure to be performed. After the appropriate combination of apparatuses has been inserted into the patient (and particularly into the kink zones and the collapse zones within the right and/or left sides of the heart), then the beating heart can be subjected to lifting and manipulation without unduly restricting the blood flow. If the beating heart blood flow is constricted or temporarily interrupted, or if a still heart surgical procedure is to be performed, the pump and cannula systems of this invention will provide supplemental or total pulmonary and/or aortic blood flow during the time that the beating heart blood flow is restricted or interrupted. Thus, this invention enables all beating heart surgical procedures without the use of a CPB machine by providing methods and apparatus systems ranging from one or more stents placed to prevent restriction of blood flow produced by the beating heart, to pump and cannula systems placed through or around the entire right side and/or through or around the entire left side to both protect the beating heart blood flow and to augment, supplement or, when necessary, temporarily replace the beating heart blood flow during the surgery. This invention thus enables various heart surgery procedures to be performed without the use of CPB machines by maintaining sufficient pulmonary blood flow through the patient's lungs (or lung) and sufficient circulatory blood flow through the patient's body to sustain the patient during the surgery.

What is claimed is:

1. A method of providing beating heart support comprising the step of
  maintaining at least partial blood flow through a protected blood flow path within a portion of at least one of the vena cava, the right atrium, the right ventricle and pulmonary artery of a beating heart,
  wherein the step of maintaining at least partial blood flow involves the step of pumping blood through said protected blood flow path by the action of the beating heart,
  wherein said protected blood flow path is established by positioning a conduit within at least one of the vena cava, the right atrium, the right ventricle, and the pulmonary artery,
  wherein said conduit is provided extending through the pulmonary valve and including a fluid inlet aperture disposed within the right ventricle,
  wherein said conduit is provided extending through the tricuspid valve and including a fluid inlet aperture disposed within the right atrium, and
  wherein said conduit is introduced into the right atrium through at least one of the inferior vena cava and the wall of the right atrium for passage through the tricuspid valve.

2. A method of proving beating heart support comprising the step of
  maintaining at least partial blood flow through a protected blood flow path within a portion of at least one of the vena cava, the right atrium, the right ventricle and pulmonary artery of a beating heart,
  wherein the step of maintaining at least partial blood flow involves the step of pumping blood through said protected blood flow path by the action of the beating heart,
  wherein a conduit is positioned at least partially within the right atrium and extending through the tricuspid valve to pre-load the right ventricle, and
  wherein said conduit is provided with a valve for preventing fluid back flow from the right ventricle into the right atrium.

3. A method of providing beating heart support comprising the step of
  maintaining at least partial blood flow through a protected blood flow path within a portion of at least one of the vena cava, the right atrium, the right ventricle and pulmonary artery of a beating heart,
  wherein the step of maintaining at least partial blood flow involves the step of pumping blood through said protected blood flow path by the action of the beating heart,
  wherein a conduit is positioned at least partially within the right atrium and extending through the tricuspid valve to pre load the right ventricle, and
  wherein said conduit is provided having at least one fluid inlet aperture disposed within the right atrium.

* * * * *